(12) United States Patent
Wildes et al.

(10) Patent No.: US 11,806,191 B2
(45) Date of Patent: Nov. 7, 2023

(54) PHASED ARRAY TRANSDUCERS AND WAFER SCALE MANUFACTURING FOR MAKING THE SAME

(71) Applicant: General Electric Company, Schenectady, NY (US)

(72) Inventors: Douglas Glenn Wildes, Ballston Lake, NY (US); Lowell Scott Smith, Schenectady, NY (US); Kwok Pong Chan, Elmhurst, NY (US); Vadim Bromberg, Schenectady, NY (US); David Martin Mills, Niskayuna, NY (US); Warren Lee, Niskayuna, NY (US); Timothy James Fiorillo, Schenectady, NY (US); Chi Tat Chiu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 1216 days.

(21) Appl. No.: 15/984,541

(22) Filed: May 21, 2018

(65) Prior Publication Data
US 2019/0350554 A1  Nov. 21, 2019

(51) Int. Cl.
*A61B 8/00* (2006.01)
*H01L 21/78* (2006.01)
(Continued)

(52) U.S. Cl.
CPC .......... *A61B 8/4488* (2013.01); *A61B 8/4494* (2013.01); *A61B 8/463* (2013.01);
(Continued)

(58) Field of Classification Search
CPC ..... H01L 21/78; H01L 27/20; H01L 41/0472; H01L 41/09; H01L 41/293; Y10T 29/42
See application file for complete search history.

(56) References Cited

U.S. PATENT DOCUMENTS 5,457,863 A * 10/1995 Thomas, III .......... B06B 1/0622
                                                29/25.35
5,735,026 A *  4/1998 Min ...................... H10N 39/00
                                                29/25.35
(Continued)

FOREIGN PATENT DOCUMENTS

EP    0663244 A2 *  7/1995  ............... B06B 1/06
EP    2637227 A1 *  9/2013  ............... A61B 8/12
(Continued)

OTHER PUBLICATIONS

Singh et al., "Additive manufacturing of PZT-5H piezoceramic for ultrasound transducers", Ultrasonics Symposium (IUS), 2011 IEEE International, pp. 1111-1114, 2011, Orlando.
(Continued)

*Primary Examiner* — Jeffrey T Carley

(57) ABSTRACT

A grid of phased array transducers includes a piezoelectric layer and a plurality of ground contact traces. The piezoelectric layer includes a first side and a second side. The plurality of ground contact traces is disposed on the first side of the piezoelectric layer along an elevational direction, where each ground contact trace of the plurality of ground contact traces extends along an azimuthal direction. Further, each phased array transducer of the grid of phased array transducers is disposed between an adjacently disposed pair of ground contact traces of the plurality of ground contact traces. Moreover, each phased array transducer includes at least a portion of at least one ground contact trace of a corresponding pair of ground contact traces, and where each phased array transducer includes a plurality of transducer elements.

10 Claims, 11 Drawing Sheets

(51) Int. Cl.
*H10N 30/20* (2023.01)
*A61B 8/08* (2006.01)
*H10N 30/063* (2023.01)
*H10N 30/87* (2023.01)
*H10N 39/00* (2023.01)

(52) U.S. Cl.
CPC ............ *A61B 8/5207* (2013.01); *H01L 21/78* (2013.01); *H10N 30/063* (2023.02); *H10N 30/20* (2023.02); *H10N 30/872* (2023.02); *H10N 39/00* (2023.02); *Y10T 29/42* (2015.01)

(56) References Cited

U.S. PATENT DOCUMENTS

| | | | |
|---|---|---|---|
| 5,757,727 A * | 5/1998 | Hanafy | B06B 1/0629 29/25.35 |
| 5,834,880 A * | 11/1998 | Venkataramani | B06B 1/064 310/334 |
| 6,492,762 B1 | 12/2002 | Pant et al. | |
| 6,656,124 B2 * | 12/2003 | Flesch | B06B 1/0622 600/459 |
| 6,685,647 B2 | 2/2004 | Savord et al. | |
| 6,776,763 B2 | 8/2004 | Nix et al. | |
| 6,894,425 B1 * | 5/2005 | Solomon | B06B 1/0629 310/334 |
| 7,908,721 B2 * | 3/2011 | Zipparo | B06B 1/0629 29/25.35 |
| 8,604,671 B2 | 12/2013 | Shikata | |
| 8,742,646 B2 | 6/2014 | Wodnicki et al. | |
| 9,293,690 B2 | 3/2016 | Sudol | |
| 9,440,259 B2 * | 9/2016 | Miyoshi | B06B 1/0688 |
| 10,347,818 B2 * | 7/2019 | Wildes | H10N 30/30 |
| 10,396,270 B2 * | 8/2019 | Arimitsu | H02N 2/163 |
| 2003/0085635 A1 * | 5/2003 | Davidsen | B06B 1/0607 310/334 |
| 2003/0193268 A1 * | 10/2003 | Junhua | H10N 30/2047 310/328 |
| 2004/0011134 A1 * | 1/2004 | Sato | A61B 8/4494 29/25.35 |
| 2005/0099096 A1 * | 5/2005 | Baumgartner | H01L 41/277 310/334 |
| 2005/0225205 A1 * | 10/2005 | Chang | H10N 30/2047 310/328 |
| 2006/0119222 A1 | 6/2006 | Sato | |
| 2013/0235123 A1 * | 9/2013 | Yokoyama | B41J 2/1643 29/25.35 |
| 2018/0272714 A1 * | 9/2018 | Nakayama | B41J 2/1609 |

FOREIGN PATENT DOCUMENTS

| | | |
|---|---|---|
| WO | 03088475 A1 | 10/2003 |
| WO | 2015145402 A1 | 10/2015 |

OTHER PUBLICATIONS

Wildes et al., "4D ICE: A 2D Array Transducer with Integrated ASIC in a 10 Fr Catheter for Real-Time 3D Intracardiac Echocardiography", IEEE Transactions on Ultrasonics, Ferroelectrics, and Frequency Control, vol. 63, Issue: 12, pp. 2159-2173, Dec. 2016.

* cited by examiner

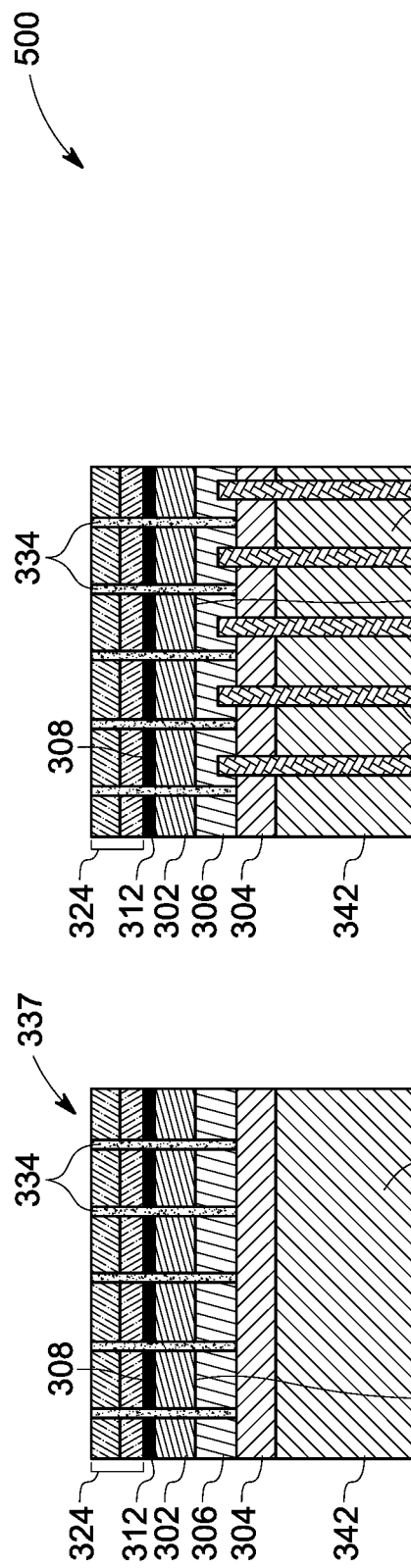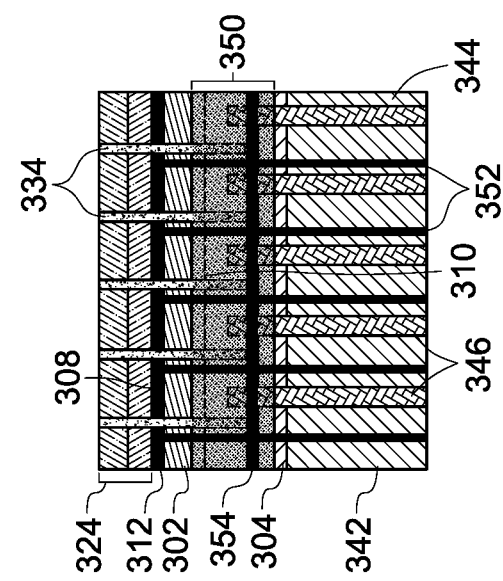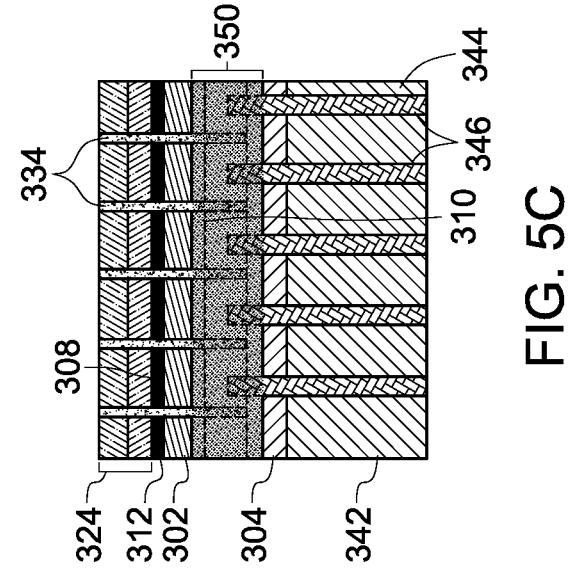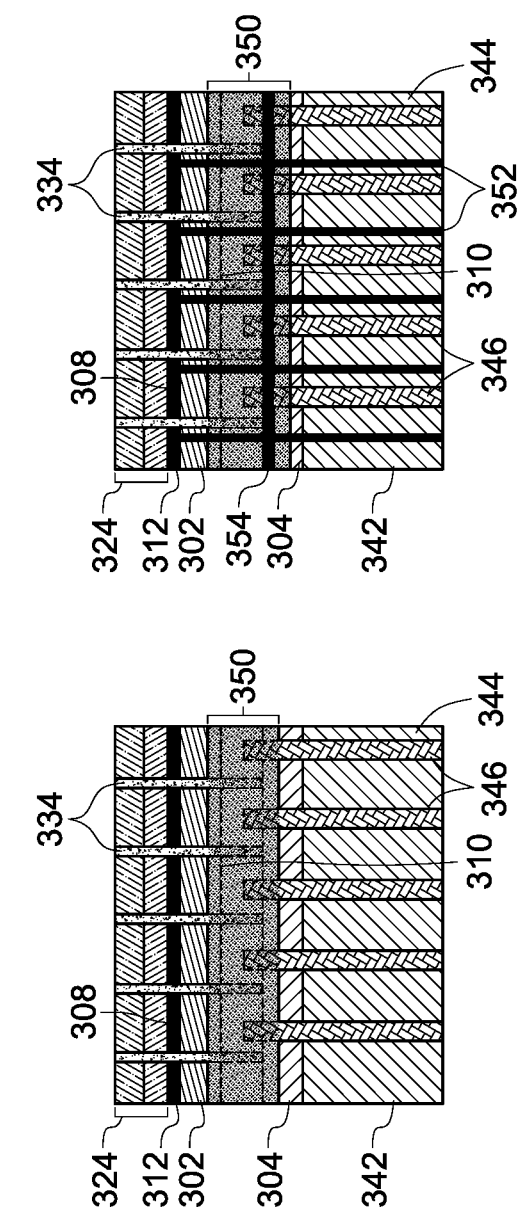

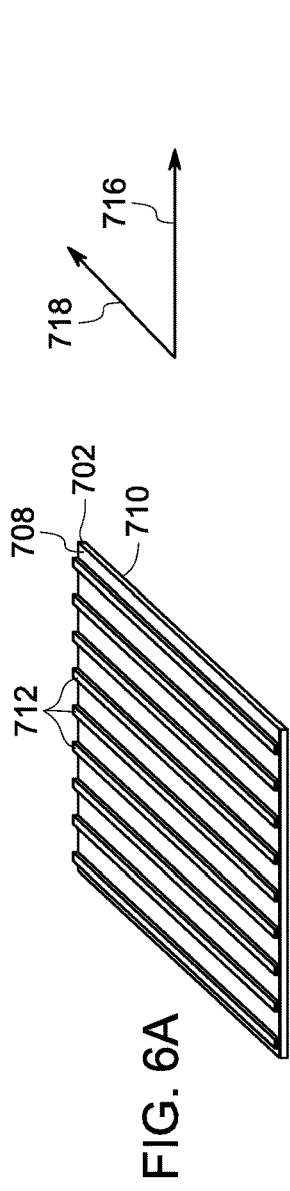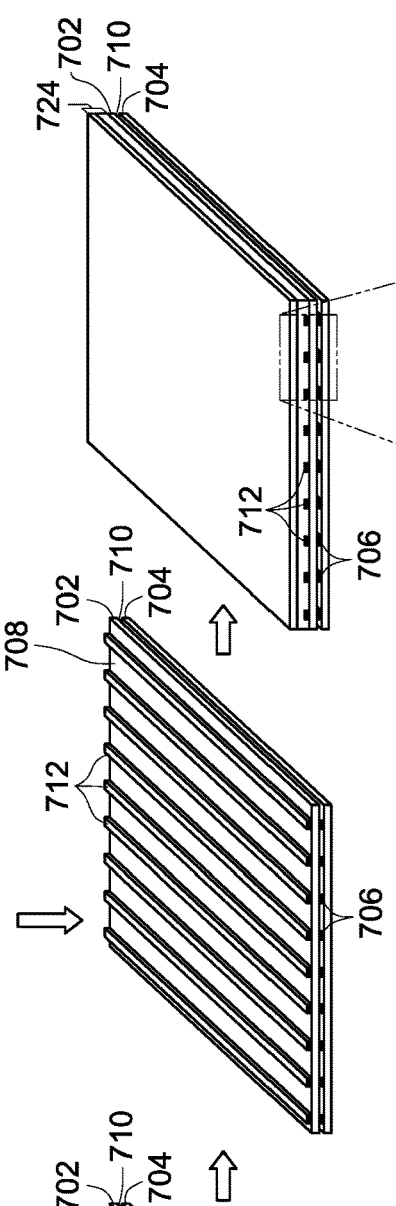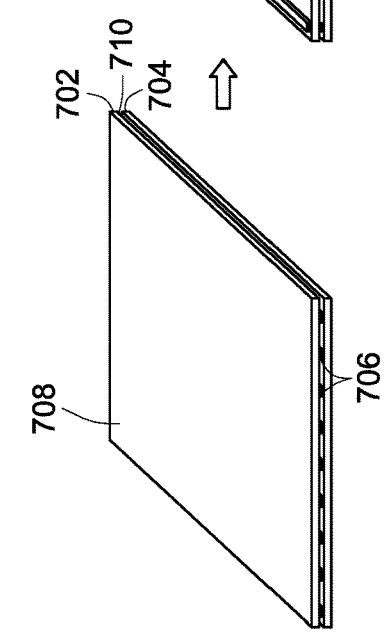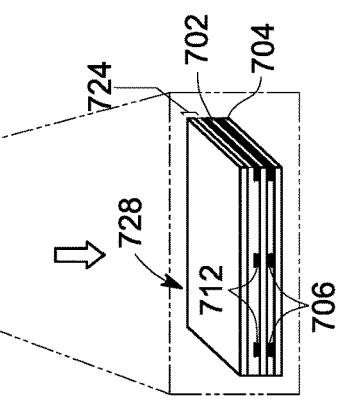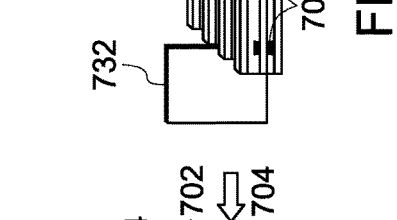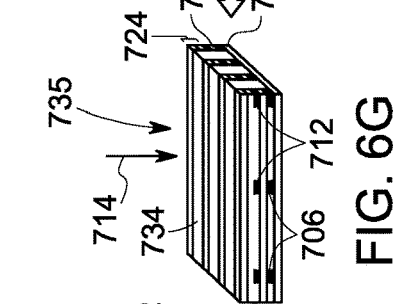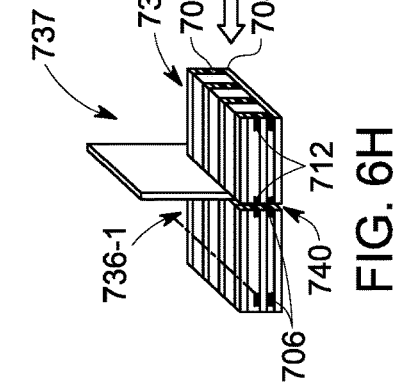

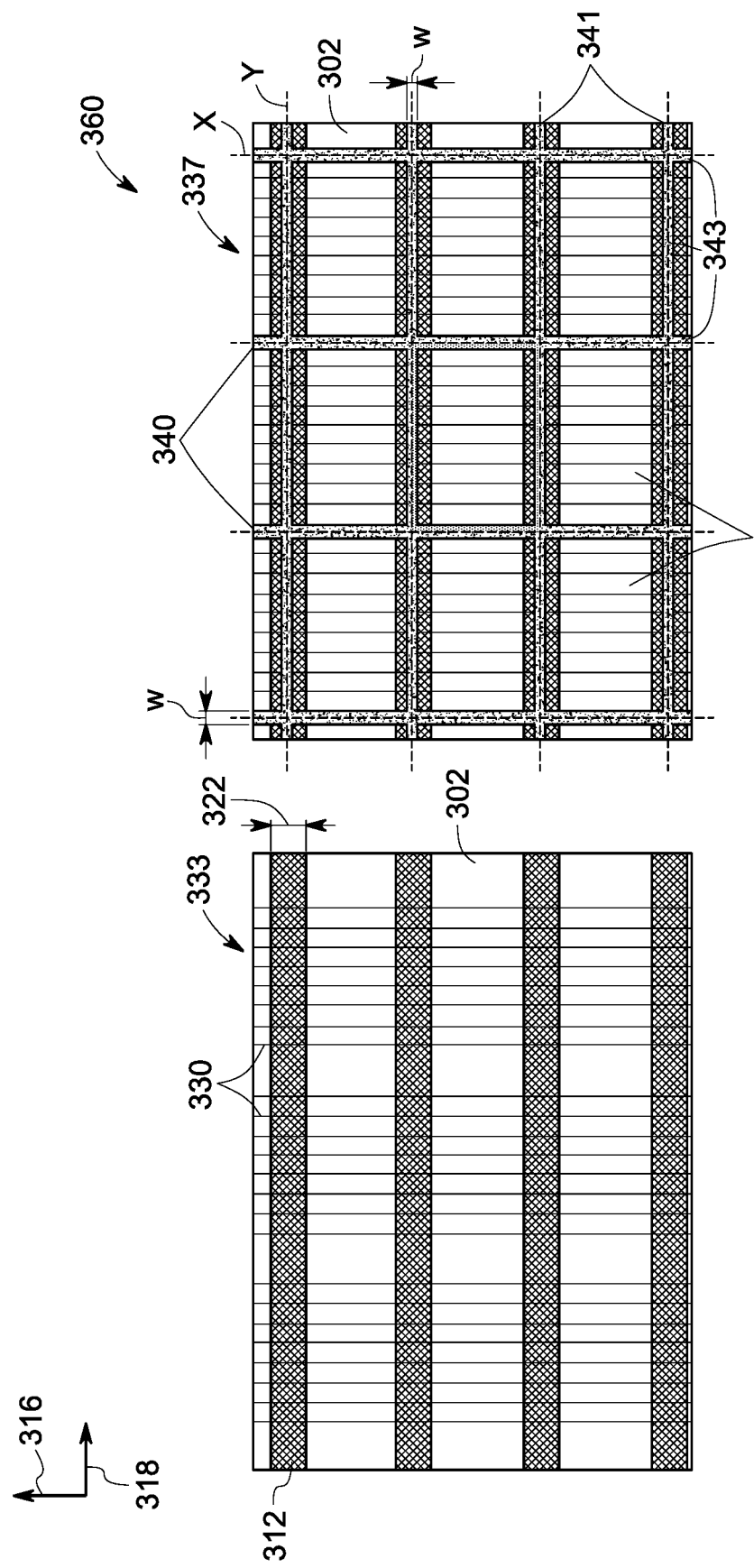

PHASED ARRAY TRANSDUCERS AND WAFER SCALE MANUFACTURING FOR MAKING THE SAME

BACKGROUND

Embodiments of the present specification relate to phased array transducers and wafer scale manufacturing for making a grid of phased array transducers.

Ultrasound is a widely used modality in medical imaging. Ultrasound imaging is typically used in cardiology, obstetrics, gynecology, abdominal imaging, and the like. Conventionally, phased array transducers are made one at a time by laminating 4 to 6 individually prepared parts. By way of example, individual layers of a piezoelectric material and one or more acoustic matching and/or de-matching materials are separately prepared by grinding the different layers one at a time to obtain respective precise thicknesses for the individual layers. Typically, for medical transducers operating between 1 to 20 MHz, thickness tolerances for these layers are only a few microns. Further, the piezoelectric material needs to be cut to a precise size down to a few microns in at least one dimension, this cut layer of the piezoelectric material is metallized with an electrode that is continuous from one surface around the edge to the opposite surface of the piezoelectric layer. This piezoelectric layer is then cut with a dicing saw to separate a ground portion of the electrode from a signal portion of the electrode. Electrical connections to transducer elements of the transducer array are typically made by a flexible printed circuit, also known as a flex circuit. After fabrication, various layers and parts are carefully cleaned and prepared, often with specific surface treatments, before adhesively bonding these layers together with epoxy.

Batch processing is desirable for manufacturing of phased array transducers, however due to design constraints such as wrap around electrodes, batch processing of the phased array transducers is possible to a very limited extent. Most parts of a phased array transducer are handled and assembled individually and tooling is designed for one transducer array per tool. Further, production lots are small, typically 1-12 transducer arrays are prepared per production lot. In many cases, the lot size is limited by the number of tools (fixtures) available. Moreover, attaining and maintaining consistent results across multiple tool sets can be a significant engineering and maintenance challenge.

Some of the currently available manufacturing processes are configured to allow fabrication of a single line of transducer arrays using appropriately long piezo material, matching layers, backing, and an appropriately wide flex circuit. However, reliance on a wrap-around electrode on the piezoelectric layer material for the ground connection requires that each finished transducer array must include at least one original edge of the piezo, which limits the manufacturing process to at most a 2×N grid of phased array transducers.

BRIEF DESCRIPTION

In one embodiment, a grid of phased array transducers includes a piezoelectric layer and a plurality of ground contact traces. The piezoelectric layer includes a first side and a second side. The plurality of ground contact traces is disposed on the first side of the piezoelectric layer along an elevational direction, where each ground contact trace of the plurality of ground contact traces extends along an azimuthal direction. Further, each phased array transducer of the grid of phased array transducers is disposed between an adjacently disposed pair of ground contact traces of the plurality of ground contact traces. Moreover, each phased array transducer includes at least a portion of at least one ground contact trace of a corresponding pair of ground contact traces, and where each phased array transducer includes a plurality of transducer elements.

In another embodiment, a grid of phased array transducers having a piezoelectric layer, one or more signal electrodes, one or more ground electrodes, and a plurality of ground contact traces is presented. The piezoelectric layer having a first side and a second side and having a plurality of transducer elements. The one or more signal electrodes are disposed on the second side of the piezoelectric layer. The one or more ground electrodes are disposed on the first side of the piezoelectric layer. The plurality of ground contact traces is disposed on at least a portion of a surface of the first side of the piezoelectric layer. The grid of phased array transducers also includes at least one of a plurality of acoustic matching layers and a de-matching layer, where the plurality of acoustic matching layers is disposed on the first side of the piezoelectric layer such that the plurality of acoustic matching layers is disposed on the plurality of ground contact traces, and where the de-matching layer is coupled to the second side of the piezoelectric layer. The grid of phased array transducers also includes an acoustic backing structure disposed on the second side of the piezoelectric layer, where the acoustic backing structure is operatively coupled to the plurality of transducer elements.

In yet another embodiment, an ultrasound system includes an acquisition subsystem, a processing subsystem, and a display device. The acquisition subsystem is configured to acquire image data, where the acquisition subsystem includes a phased array transducer. The phased array transducer includes a piezoelectric layer having a first side and a second side and having a plurality of transducer elements. The phased array transducer also includes one or more ground electrodes disposed on the first side of the piezoelectric layer, and one or more signal electrodes disposed on the second side of the piezoelectric layer. Further, the phased array transducer includes a plurality of ground contact traces disposed on at least a portion of a surface of the piezoelectric layer, and an acoustic backing structure operatively coupled to the plurality of transducer elements. The ultrasound system includes also includes a processing subsystem coupled to the acquisition subsystem and configured to process the acquired image data; and a display device configured to display the acquired image data, the processed image data, or both.

In another embodiment, a wafer scale method for manufacturing a grid of phased array transducers includes providing a piezoelectric layer having a first side and a second side. The method further includes forming a plurality of ground contact traces along an elevational direction on the first side of the piezoelectric layer to define an acoustic array stack, where each of the plurality of ground contact traces extends along an azimuthal direction. The method also includes dicing the acoustic array stack along an elevational direction perpendicular to the ground contact traces to define individual transducer elements that are electrically isolated from one another. Further, the method includes dicing the acoustic array stack along the azimuthal direction through the ground contact traces to define strips of phased array transducers such that at least a portion of each of the plurality of ground contact traces is exposed along a side of the strips of the phased array transducers, and coupling a carrier block to at least a portion of the acoustic array stack.

DRAWINGS

These and other features and aspects of embodiments of the invention will become better understood when the following detailed description is read with reference to the accompanying drawings in which like characters represent like parts throughout the drawings, wherein:

FIGS. 5A-5D are cross-sectional side views viewed along an elevational direction and illustrating method steps subsequent to the step represented by FIG. 3G for manufacturing the grid of phased array transducers, in accordance with aspects of the present specification;

FIGS. 6A-6L are schematic representations of a wafer scale method of manufacturing a grid of phased array transducers, in accordance with aspects of the present specification;

Figure 8:
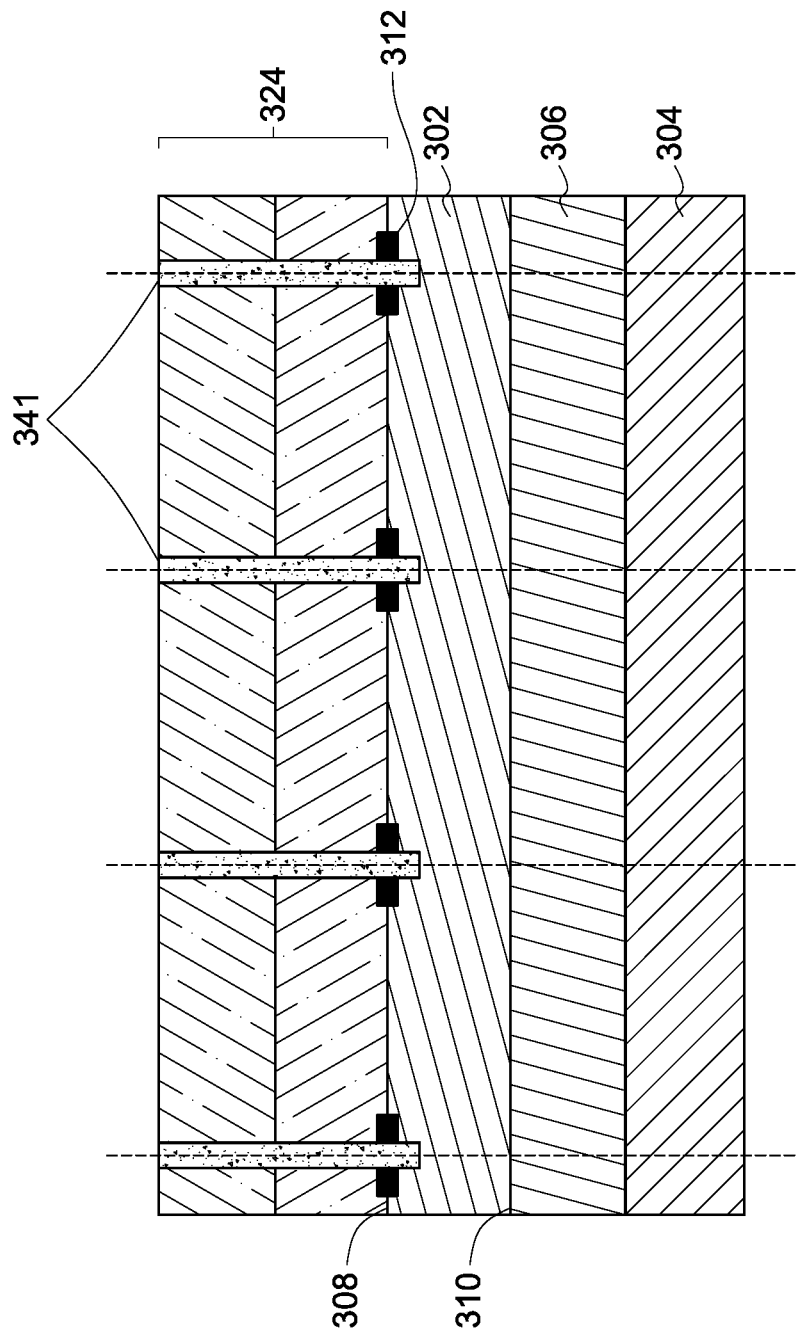
Figure 9B:
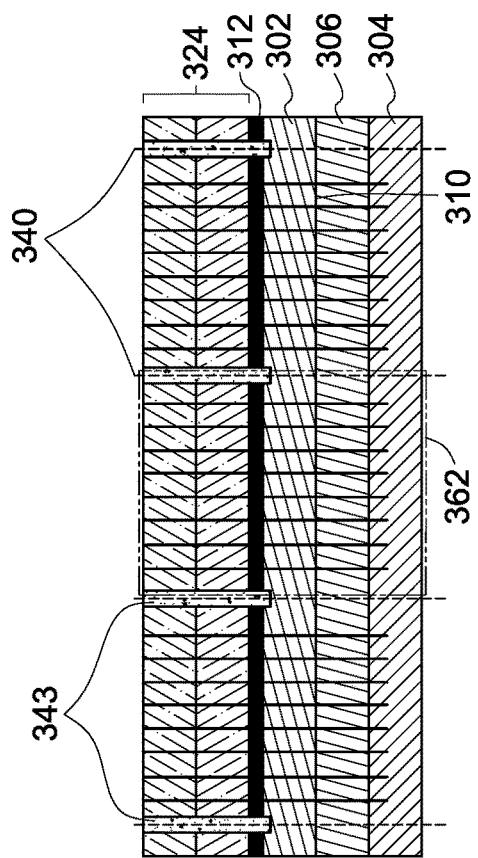
Figure 9A:
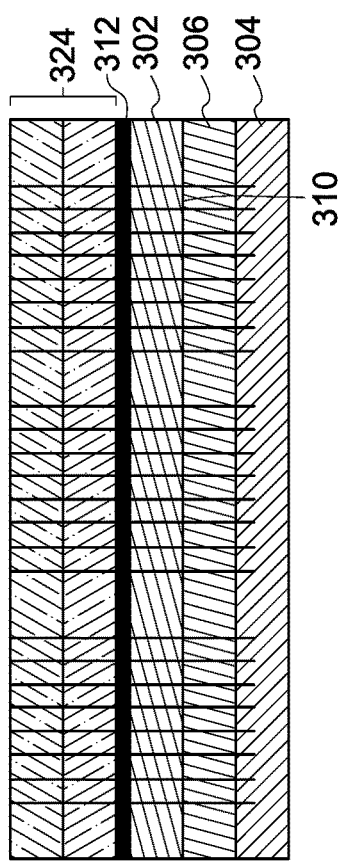
Figure 11:
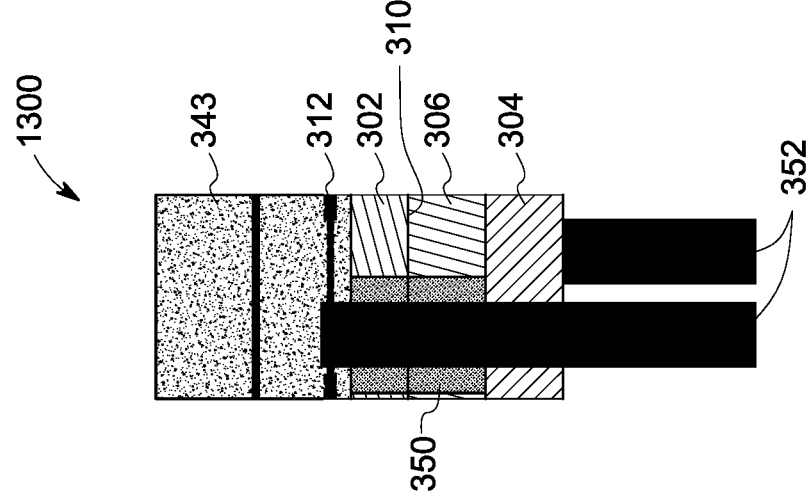
Figure 10:
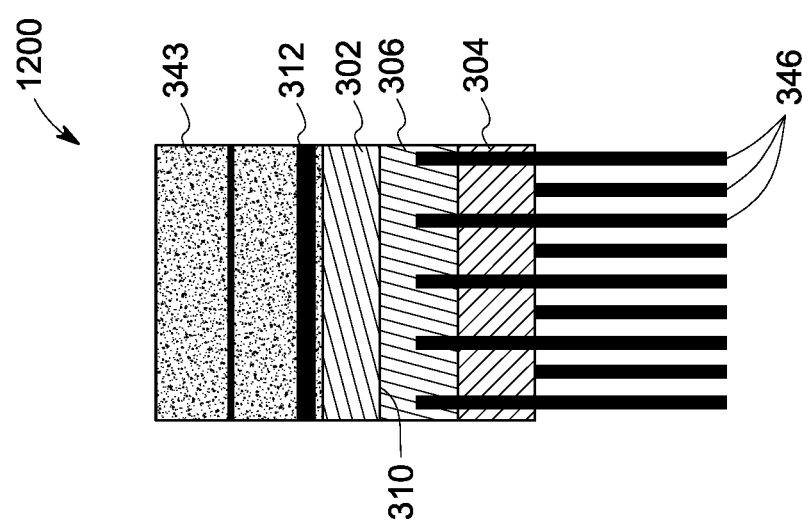

FIGS. 7A-7B, 8, and 9A-9B are schematic representations of a wafer scale manufacturing process for forming a grid of phased array transducers having a de-matching layer and a boundary ground bus; and FIGS. 10-11 are schematic representations of a phased array transducer formed using the method of FIGS. 7A-7B and 9A-9B.

DETAILED DESCRIPTION

Embodiments of the present specification relate to phased array transducers and wafer scale manufacturing for making arrays of such phased array transducers. The wafer scale manufacturing of the present specification enables batch processing of phased array transducers to fabricate a grid of phased array transducers (PATs). In certain embodiments, at least for some method steps, the wafer scale manufacturing employs additive manufacturing methods for forming the grid of phased array transducers.

As used herein, the terms "grid of phased array transducers," "grid of phased array ultrasound transducers," and "grid of PATs" are used interchangeably throughout the present specification, and refer to a grid of individual phased array transducers. Further, it may be noted that the terms "phased array transducer," "PAT," and "phased array ultrasound transducer" are used interchangeably throughout the present specification, and refer to an array of transducer elements. Moreover, it may be noted that a transducer element is a smallest individually addressable unit of a phased array transducer (PAT).

In certain embodiments, after disposing determined layers, such as piezoelectric layers, acoustic matching layers, a carrier block (for example, an acoustic backing structure), and the like, electrical traces are provided on the surface of the carrier block to enable electrical coupling between a plurality of transducer elements of each phased array transducer or each phased array transducer and driving circuitry of an ultrasound system employing each of the phased array transducers. The plurality of electrical traces includes a plurality of signal traces and a plurality of ground traces. The electrical traces are routed on the carrier block such that there is electrical isolation between the individual signal traces, and between the signal traces and one or more electrodes of the phased array transducer.

Although, the exemplary embodiments illustrated hereinafter are described in the context of a carrier block for use in a medical imaging system such as an ultrasound imaging system, it will be appreciated that use of such a carrier block in an ultrasound imaging system in other applications such as equipment diagnostics and inspections, baggage inspections, security applications are also envisaged.

Figure 1:
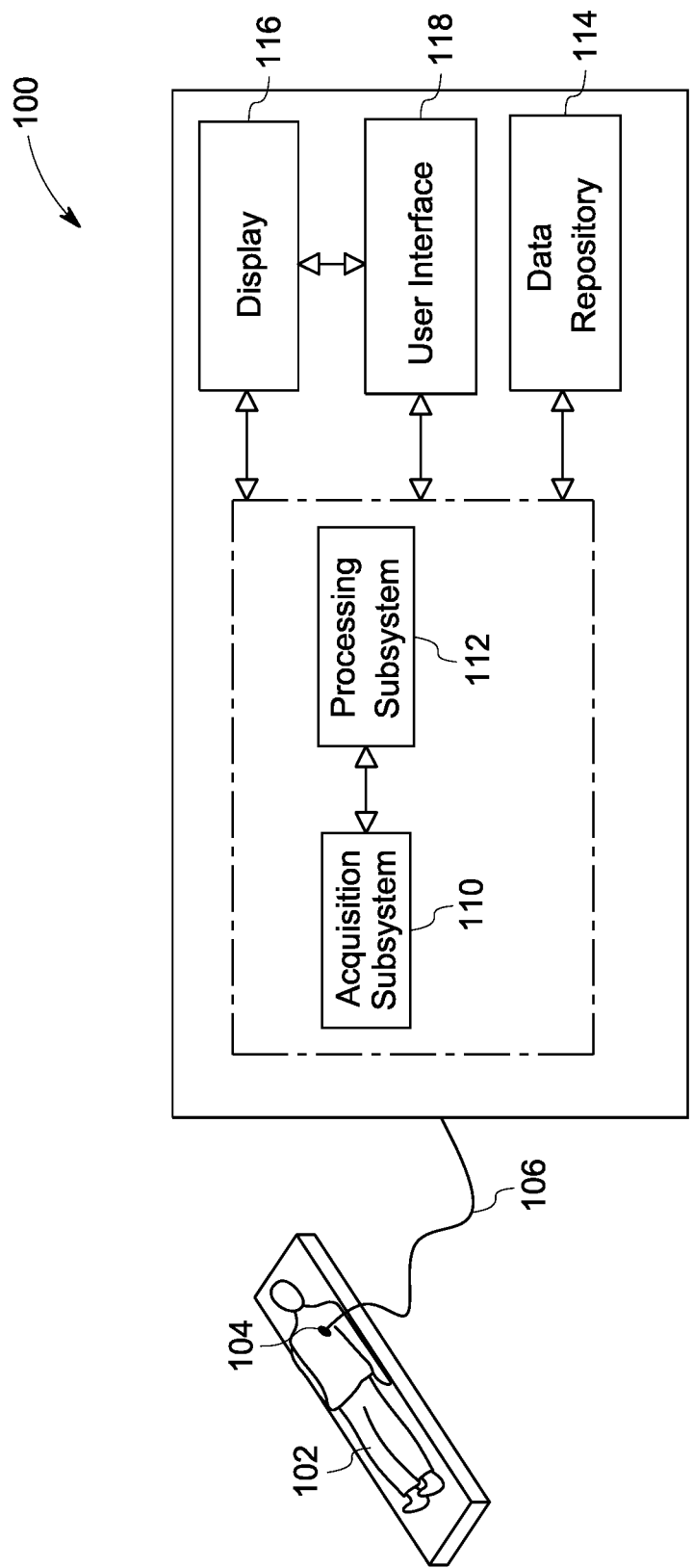
FIG. 1 is a diagrammatical illustration of an exemplary ultrasound system, in accordance with aspects of the present specification.

FIG. 1 illustrates an exemplary medical imaging system, such as an ultrasound system 100, for use in imaging, in accordance with aspects of the present specification. The system 100 is configured to facilitate acquisition of image data from an object of interest such as a patient 102 via an ultrasound transducer probe 104, for example. However, in certain other embodiments, the object of interest may include luggage, a sample, other equipment, and the like. The probe 104 may be configured to acquire image data representative of a region of interest in the patient 102. In some embodiments, the probe 104 may be configured to facilitate interventional procedures. Accordingly, in these embodiments, the probe 104 may include an invasive probe. In some other embodiments, the probe 104 may include a non-invasive probe. In the present non-limiting example of FIG. 1, the object of interest includes a patient 102 and the ultrasound transducer probe 104 is a non-invasive probe. Non-limiting examples of the probe 104 may include a transthoracic probe, endoscopes, laparoscopes, catheter-based probes, surgical probes, transrectal probes, transvaginal probes, intracavity probes, probes adapted for interventional procedures, other external probes, or combinations thereof. The probe 104 houses a phased array transducer (not shown in FIG. 1). The phased array transducer includes a plurality of transducer elements (not shown in FIG. 1).

In certain embodiments, the probe 104 may include an imaging catheter-based probe. Further, an imaging orientation of the imaging catheter may include a forward viewing catheter, a side viewing catheter, or an oblique viewing catheter. However, a combination of forward viewing, side viewing and oblique viewing catheters may also be employed as the imaging catheter.

Reference numeral 106 represents an electrical cable that connects the probe to other components of the ultrasound system 100. The electrical cable 106 provides electrical connection between the phased array transducer and driving circuitry (not shown in FIG. 1) of the system 100. Specifically, the cable 106 provides the electrical connection between the plurality of transducer elements of the phased array transducer and the driving circuitry of the system 100.

In embodiments of the present specification, the phased array transducer is manufactured using wafer scale manufacturing applied to a piezoelectric wafer or layer to form a grid of phased array transducers. The phased array transducer used in the embodiment of FIG. 1 may be one such phased array transducer of the grid of phased array transducers manufactured using the wafer scale manufacturing. The representative phased array transducer of FIG. 1 includes a piezoelectric layer having a first side and a second side. In certain embodiments, the grid of the phased array transducers includes a plurality of ground contact traces, and one or both of acoustic matching layers and a de-matching layer. The plurality of ground contact traces is disposed on the first side of the piezoelectric layer along an elevational direction. Further, each ground contact trace of the plurality of ground contact traces extends along an azimuthal direction.

In some embodiments, the grid of phased array transducers may include a plurality of acoustic matching layers disposed on the first side of the piezoelectric layer such that the plurality of acoustic matching layers is disposed on the plurality of ground contact traces. In these embodiments, areas of the piezoelectric layer disposed adjacent to the ground contact traces are in physical contact with the acoustic matching layers. Particularly, in addition to being disposed on the ground contact traces, material of the acoustic matching layer fills up adjacent areas on the piezoelectric layer. In some other embodiments, the ground contact traces themselves may be configured to act as one or more of the plurality of acoustic matching layers, such as at least the first of the plurality of acoustic matching layers. In these embodiments, a separate plurality of acoustic matching layers may not be used to form the grid of phased array transducers. In some embodiments, a combination of the plurality of ground contact traces disposed on the first side of the piezoelectric wafer may be used in conjunction with one or more de-matching layers that are disposed on the second side of the piezoelectric layer. In some of these embodiments, the acoustic matching layers may not be present in the grid of phased array transducers. When employed, the de-matching layers may be disposed between an acoustic backing structure of the grid of phased array transducers and the second side of the piezoelectric layer.

In the grid of phased array transducers, each phased array transducer is disposed between a pair of ground contact traces of the plurality of ground contact traces. When separated from the grid of phased array transducers, each individual phased array transducer includes at least a portion of at least one ground contact trace of the corresponding pair of ground contact traces. In a non-limiting example, each individual phased array transducer includes portions of adjacently disposed pairs of ground contact traces of the plurality of ground contact traces.

Further, each phased array transducer of the grid of phased array transducers includes a plurality of transducer elements that is disposed as an array of transducer elements. The transducer elements are configured to generate and transmit acoustic energy to the patient 102. Further, the plurality of transducer elements is also configured to receive backscattered acoustic signals from the patient 102 to create and display an image. In addition to the piezoelectric layer, and the one or more acoustic matching layers, each phased array transducer also includes a lens, the acoustic backing structure, and a plurality of electrical traces routed on a surface of the acoustic backing structure. The acoustic backing structure may be present in the form of a highly attenuative backing structure for attenuating acoustic waves. Further, in some instances, one or more de-matching layers may be disposed between the piezoelectric layer and the acoustic backing structure. Additionally, in some instances, an interconnect circuit or interposer may be disposed between the de-matching layer (if present) or piezoelectric layer and the acoustic backing structure. The interposer circuit is configured to operatively couple the phased array transducer to the driving circuit of the system 100 via the acoustic backing structure. Additionally, the lens may be disposed on an acoustic matching layer and configured to provide an interface between the patient 102 and the matching layer. In certain embodiments, the lens may be configured to direct and focus acoustic energy transmitted by the transducer elements of the phased array transducer to the patient 102. Alternatively, the lens may include a non-focusing layer. The acoustic matching layers may be configured to facilitate matching of an impedance differential that may exist between the high impedance transducer elements and the low impedance patient 102.

In some embodiments, the electrical traces are routed on the acoustic backing structure in a conformal manner using additive manufacturing. As used herein, the term "conformal manner," "conformally deposited," or "conformally routed" refers to deposition of electrical traces using additive manufacturing on a surface of the acoustic backing structure such that the electrical traces follow one or more contours, turns, curvature, edges, and surface profiles of the surface of the acoustic backing structure on which the electrical traces are disposed.

The system 100 may be in operative association with the probe 104 and configured to facilitate acquisition and/or processing of image data. To that end, the system 100 may include an acquisition subsystem 110 and a processing subsystem 112. The image data acquired and/or processed by the system 100 may be employed to aid, for example, a clinician, in identifying disease states, assessing need for treatment, determining suitable treatment options, tracking the progression of the disease, and/or monitoring the effect of treatment on the disease states.

Although not illustrated in FIG. 1, the acquisition subsystem 110 also includes transmit/receive switching circuitry, a transmitter, a receiver, and a beamformer. In certain embodiments, the plurality of transducer elements is arranged in a spaced relationship to form a phased array transducer, such as, but not limited to, a one-dimensional or a two-dimensional phased array transducer.

When ultrasound waves are transmitted into the patient 102, the ultrasound waves are backscattered off the tissue and blood within the patient 102. The phased array transducer receives the backscattered waves at different times, depending on the distance into the tissue the waves return from and the angle with respect to the surface of the transducer assembly at which the waves return. The transducer elements convert the ultrasound energy from the backscattered waves into electrical signals. In one embodiment, the transducer assembly may be a two-way transducer, where each transducer element operates as both a transmitter and receiver.

In certain embodiments, the processing subsystem 112 may be coupled to a storage system, such as the data repository 114, where the data repository 114 is configured to store the acquired image data. Although not illustrated, the processing subsystem 112 may include a control processor, a demodulator, an imaging mode processor, a scan converter, and a display processor. In one example, the display processor may be coupled to a display monitor/device 116 for displaying images. User interface 118 may be used to interact with the control processor and the display monitor/device 116. The control processor may also be coupled to a remote connectivity subsystem including a web server and a remote connectivity interface. The processing subsystem 112 may be further coupled to data repository, such as the data repository 114, and configured to receive ultrasound image data. The data repository 114 interacts with an imaging workstation.

Further, the system 100 may be configured to display the acquired image data using the display device 116 and the user interface area 118. In accordance with aspects of the present specification, the display device 116 may be configured to display the image generated by the system 100 based on the image data acquired via the imaging probe 104. Additionally, the display device 116 may be configured to aid the user in visualizing the generated image. In certain embodiments, such as in a touch screen, the display device 116 and the user interface 118 may overlap.

Aforementioned components of an ultrasound imaging system, such as the system 100, may be dedicated hardware elements such as circuit boards with digital signal processors or may be software running on a general-purpose computer or processor such as a commercial, off-the-shelf personal computer (PC). The various components may be combined or separated according to various embodiments of the present specification. Thus, as will be appreciated, the present ultrasound imaging system, such as the system 100, is provided by way of example, and the present systems and methods are in no way limited by the specific system configuration. Further, although the exemplary embodiments illustrated hereinafter are described in the context of a medical imaging system, such as an ultrasound imaging system, other imaging systems and applications such as industrial imaging systems and non-destructive evaluation and inspection systems, such as pipeline inspection systems, liquid reactor inspection systems are also contemplated. For example, the exemplary embodiments illustrated and described hereinafter may find application in industrial borescopes that are employed for thickness monitoring, interface monitoring, or crack detection. Additionally, the exemplary embodiments illustrated and described hereinafter may find application in multi-modality imaging systems that employ ultrasound imaging in conjunction with other imaging modalities, position-tracking systems or other sensor systems. Moreover, applications directed toward stimulation and therapeutic purposes are also envisioned within the purview of the present specification. Therapeutic applications may include, but are not limited to, high intensity focused ultrasound (HIFU), lithotripsy, targeted ultrasound drug delivery, ultrasound assisted thrombolysis. Stimulation applications may include, but are not limited to, neural or sensory stimulation.

Advantageously, the systems and methods described in this application may be employed in the manufacturing processes of existing ultrasound transducer probes with minimal or no modification required in components of the existing ultrasound transducer probes. Further, as the methods of the present specification enable wafer scale manufacturing of phased array transducers, the phased array transducers so manufactured may have lower fabrication and material costs, thereby reducing the overall cost of the phased array transducers. Moreover, the wafer scale manufacturing method of the present specification advantageously eliminates or substantially reduces laminations and other manual processes, so should be conducive to low-cost, high-volume, and high-yield manufacturing. Most features of the resulting arrays (for example, size, number of elements, pitch, matching layer thicknesses) are defined by programmable machine parameters, so a single manufacturing line can be quickly reconfigured to produce different arrays, and the number and variety of purchased components (that is, inventory cost) is greatly reduced.

Further, in certain embodiments, the methods of the present specification may employ one or more additive manufacturing techniques that may provide enhanced control over dimensions of individual layers, and may not require adhesive layers to be present between each pair of layers in the grid of phased array transducers. By way of example, an adhesive may not be required between the acoustic matching layers and the piezoelectric layer, where one layer is directly deposited or printed on the other layer.

In certain embodiments, the phased array transducer may be made using wafer scale manufacturing, in which an array of such phased array transducers may be manufactured using one or more additive manufacturing techniques and other deposition techniques. Accordingly, in some of these embodiments, suitable materials are deposited, usually layer upon layer, to make three-dimensional objects. Various exemplary methods of additive manufacturing usable with the present specification may include processes, such as, but not limited to, direct write, electron beam deposition, laser deposition, stereo-lithography, three-dimensional (3D) printing, and combinations thereof.

Figure 2:
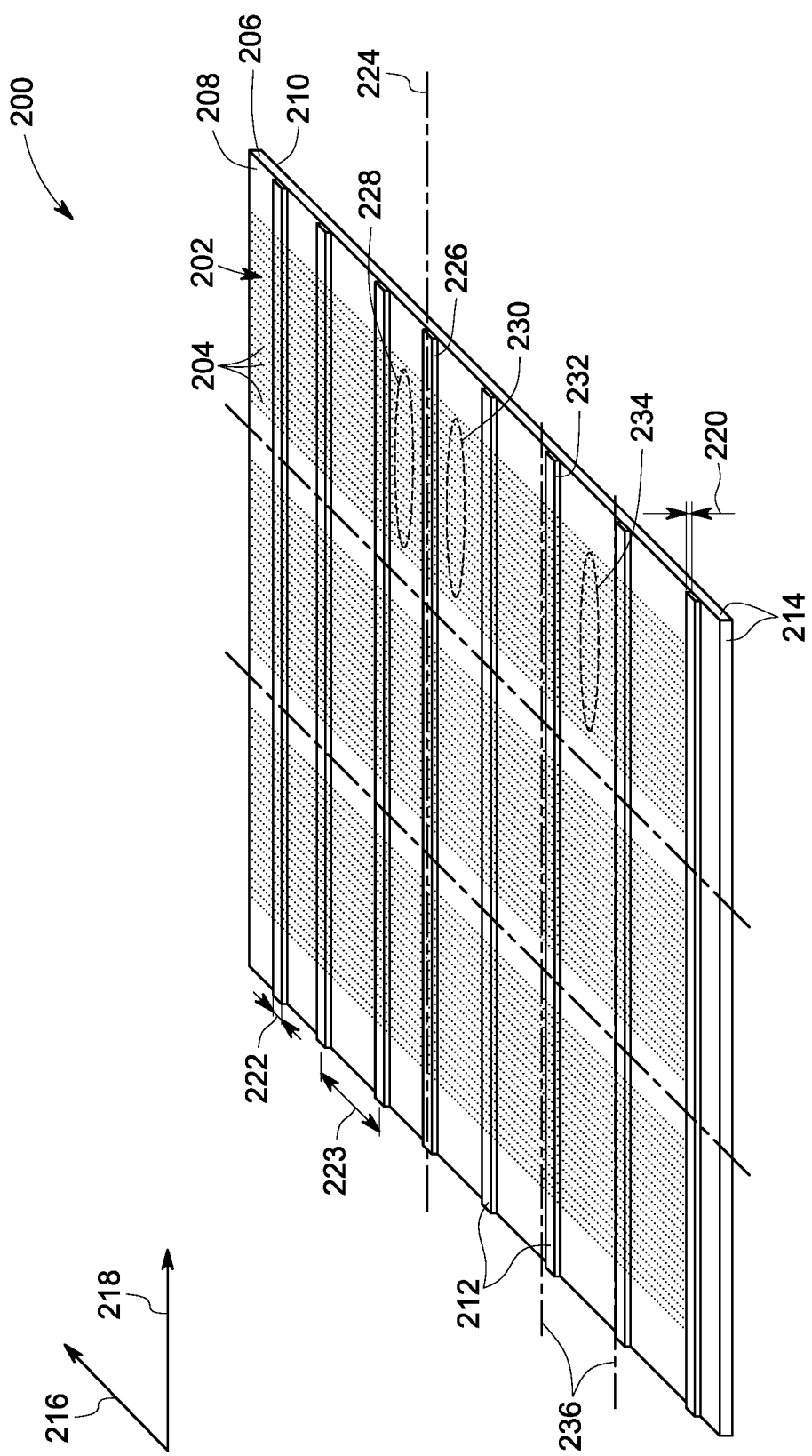
FIG. 2 is a perspective view of a grid of phased array transducers prior to attaching a carrier block and forming desired electrical connections, in accordance with aspects of the present specification.

FIG. 2 is a perspective view 200 of a grid of phased array transducers prior to attaching a carrier block and forming desired electrical connections. In particular, FIG. 2 illustrates a piezoelectric layer 206 having a metallized first side 208 and a metallized second side 210. It should be noted that metallized surfaces 208 and 210 of the piezoelectric layer 206 form the ground and signal electrodes (not shown in FIG. 2), respectively. In the illustrated embodiment, the ground electrode is a thin layer of metal disposed on the first side 208 of the piezoelectric layer 206. The signal electrodes are a thin layer of metal disposed on the second side 210 of the piezoelectric layer 206. The reference numerals 208 and 210 are used to represent the metallized sides 208 and 210 having the thin metal electrodes, which form the ground and signal electrodes, respectively. The metallized sides 208 and 210 are generally referred to as first and second sides 208 and 210, respectively, throughout the present specification. The first and second sides 208 and 210 of the piezoelectric layer 206 may be metallized by sputtering, evaporating, electro-less plating, electroplating, or the like to form the thin metal electrodes of the sides 208 and 210. The piezoelectric layer 206 may be a wafer scale layer having dimensions suitable for forming a desirable size of a grid of phased array transducers (not shown in FIG. 2). The grid of phased array transducers may be manufactured using wafer scale manufacturing. In certain embodiments, the wafer scale manufacturing may include additive manufacturing. The grid of phased array transducers includes individual phased array transducers generally represented by reference numeral 202. Further, each individual phased array transducer 202 includes a plurality of transducer elements, generally represented by reference numeral 204.

A plurality of ground contact traces 212 is disposed on the first side 208 of the piezoelectric layer 206. The ground contact traces 212 are electrically conductive traces that are formed on the first side 208 of the piezoelectric layer 206 to provide electrical connection between the thin metal electrodes disposed on the first side 208 of the piezoelectric layer 206 and a plurality of electrical traces (not shown in FIG. 2). In one embodiment, the ground contact traces 212 may be disposed parallel to one another. Further, the ground contact traces 212 are disposed along an elevational direction 216 of the piezoelectric layer 206. Moreover, each ground contact trace 212 extends along an azimuthal direction 218 of the piezoelectric layer 206.

In some embodiments, the ground contact traces 212 may be additively manufactured on the metallized first side 208 of the piezoelectric layer 206. In alternative embodiments, the ground contact traces 212 may be deposited using other deposition techniques, such as sputtering, physical vapor deposition, chemical vapor deposition, atomization, and the like. The ground contact traces 212 may have a thickness 220 of about 5 microns to about 50 microns. Further, the ground contact traces 212 may have a width 222 of about 20 to about 2000 microns. Widths 222 of the various ground contact traces 212 may be the same or different. Dimensions, such as the thickness 220 and the width 222 of the ground contact traces 212 may be selected to facilitate electrical connections between the ground contact traces 212 and the electrical traces. It should be noted that the width 222 of the ground contact traces 212 should be lower than the distance between two adjacently disposed ground contact traces 212. Further, the width 222 of the ground contact traces 212 should be thin enough to not significantly perturb acoustic performance of transducer elements of the individual phased array transducer 202. In certain embodiments, the width 222 of the ground contact traces 212 is less than 10% of the distance 223 between any two adjacently disposed ground contact traces 212. Further, the width 222 (and the thickness 220) of the ground contact traces 212 are such that the electrical resistance of an individual ground contact trace 212 is large enough to achieve a trace resistance that contributes less than 2% to a radiation resistance of the transducer elements. In one embodiment, the contribution of the trace resistance toward the radiation resistance is in a range from about 1% to about 2%. In one example, the width 222 of a ground contact trace 212 is 0.2 mm, and distance 223 between two adjacent ground contact traces 212 is in a range of 3 mm to 13 mm In a non-limiting example, where a width 222 of the ground contact trace 212 is 0.2 mm and a distance 223 between the ground contact traces 212 is 3 mm, the area impact of the ground contact trace 212 is 6.7%. Similarly, in another non-limiting example, an area impact of the ground contact trace 212 having a width 222 of 0.2 mm and a distance 223 of 13 mm is only 1.5%.

Presence of the ground contact traces 212 on at least a portion of a surface of the first side 208 of the piezoelectric layer 206 obviates the need for wrapping conventionally formed ground connections around an edge 214 of the piezoelectric layer 206. As will be appreciated, conventionally formed ground connections are continuous from one surface around the edge to the opposite surface of the piezoelectric layer 206. The design of conventional phased array transducers where ground connections are wrapped around the piezoelectric layer makes it difficult to manufacture arrays other than 2×N arrays as each transducer needs to have at least one original edge of the piezoelectric layer. Hence, conventional designs of the phased array transducers prohibit forming phased array transducers at a mass scale, for example, in a batch processing. In particular, the conventional designs of the phased array transducers are limited to 2×N size.

As will be appreciated, the grid may include any N×M grid of at least 4 to 100 transducers depending on a size of the original wafer of the piezoelectric layer 206 and desirable sizes of individual phased array transducers that are to be formed using the piezoelectric layer 206. In the grid of the phased array transducers 202, each pair of neighboring transducers 202 disposed along the elevational direction 216, shares a common ground contact trace 212. As illustrated by the dashed line 224, in one embodiment, one of the ground contact traces 226 of the ground contact traces 212 may be cut along its width 222 between neighboring phased array transducers 228 and 230. In another embodiment, entire width 222 of a ground contact trace 232 may belong to a corresponding phased array transducer 234. In the illustrated example, the phased array transducer 234, when separated from the grid of phased array transducers 202 includes a ground contact trace 232 disposed on only one side. The side of the phased array transducer 234 disposed opposite to the ground contact trace 232 may not include a ground contact trace as represented by separation lines 236.

FIGS. 3A-3G illustrate a method flow diagram 300 of wafer scale manufacturing of a grid of phased array transducers, in accordance with embodiments of the present specification. The method starts by providing a piezoelectric layer 302 having an acoustic backing wafer 304. The acoustic backing wafer 304 may be configured to provide mechanical stability to the piezoelectric layer 302. Optionally, a de-matching layer 306 may be present between the piezoelectric layer 302 and the backing wafer 304. The acoustic backing wafer 304 forms an acoustic backing structure in the phased array transducers formed using the method of FIGS. 3A-3G.

The piezoelectric layer 302 may be made of a single crystal piezoelectric material or may be made of a piezoelectric ceramic material and have a suitable thickness. In certain embodiments, the transducer elements may be fabricated employing piezoelectric or micro-machined electromechanical (MEMS) materials, such as but not limited to, lead zirconate titanate (PZT), lead magnesium niobate titanate (PMNT), composite PZT, or micro-machined silicon. In one example, the piezoelectric layer 302 includes a lead zirconate titanate (PZT) layer. In another example, the piezoelectric layer 302 may include binary piezoelectric $(1-x)Pb(Mg_{1/3}Nb_{2/3})O_3\text{-}xPbTiO3$ (PMNT) crystals or ternary piezoelectric $Pb(In_{1/2}Nb_{1/2})O_3\text{---}Pb(Mg_{1/3}Nb_{2/3})O_3\text{-}xPbTiO_3$ (PIMNT) crystals. The piezoelectric layer 302 may have a thickness that is greater initially than it is in the finished form. In one embodiment, the piezoelectric layer 302 undergoes a grinding and/or lapping process on one or both surfaces.

Further, surfaces or faces of first and second sides 308 and 310, respectively, of the piezoelectric layer 302 are metallized to form thin metal electrodes that act as ground and signal electrodes (not shown in FIGS. 3A-3G). Particularly, a thin electrode (not shown in FIGS. 3A-3G) disposed on the first side 308 of the piezoelectric layer 302 is the ground electrode, and another thin electrode (not shown FIGS. 3A-3G) disposed on the second side 310 of the piezoelectric layer 302 is the signal electrode. As with the ground and signal electrodes present on the first and second sides 208 and 210 of the piezoelectric layer 206 in FIG. 2, the ground and signal metal electrodes present on first and second sides 308 and 310 of the piezoelectric layer 302 may be formed using one or more standard metallization techniques (such as sputtering, plating) and/or additive manufacturing or three-dimensional (3D) printing processes (such as controlled dispensing, jetting, and so forth) and curing of a highly conductive ink (e.g., nanoparticle- or organometallic-based silver, copper, or gold) on the first and second sides 308 and 310 of the piezoelectric layer 302. In one example, for depositing the ground and/or signal electrodes, an adhesion layer may be sputter deposited followed by a sputtered layer of metal, such as gold. Size of the piezoelectric layer 302 may be determined based on the number and size of individual phased array transducers that are to be formed on the piezoelectric layer 302.

Optionally, the de-matching layer 306 may be coupled to the second side 310 of the piezoelectric layer 302. The de-matching layer 306 may include electrically conductive material having high acoustic impedance. Non-limiting examples of the materials for the de-matching layer 306 include tungsten carbide or other suitable materials that function as a node-material that acts to change the effective resonant frequency generated by the piezoelectric material of the piezoelectric layer 302. Presence of the de-matching layer 306 and its effect on the resonant frequency of the piezoelectric layer 302 allows a thinner piezoelectric layer 302 to be employed while still obtaining the desired range of frequencies.

A size of the de-matching layer 306 may be same as or larger than the size of the piezoelectric layer 302. In some embodiments, a pre-formed de-matching layer 306 may be coupled to the second side 310 of the piezoelectric layer 302. Alternatively, in some other embodiments, the de-matching layer 306 may be directly formed, such as deposited using known deposition techniques, for example, plating and/or cold spray, or additively manufactured, such as printed, on the second side 310 of the piezoelectric layer 302.

Again, the acoustic backing wafer 304 may be disposed on the de-matching layer 306, or directly on the second side 310 of the piezoelectric layer 302. The acoustic backing wafer 304 is made of materials having suitable acoustic and mechanical properties. Further, the acoustic backing wafer 304 may have a suitable thickness to provide mechanical strength to the resultant phased array transducer. The material of the acoustic backing wafer 304 may include a composite material having acoustic scattering materials or particles, such as, but not limited to, tungsten particles, phenolic microspheres, and the like. Further, the acoustic backing wafer 304 may also include acoustic absorbing rubber, such as, room-temperature vulcanizing (RTV), and silicone granules. The composite material may include a structural matrix made of an epoxy. The acoustic backing wafer 304 may be a pre-formed structure that is coupled to the piezoelectric layer 302. Alternatively, the acoustic backing wafer 304 may be directly formed, such as deposited using known deposition techniques, or additively manufactured, such as printed, on the de-matching layer 306 or the second side 310 of the piezoelectric layer 302. A size of the acoustic backing wafer 304 may be same as or larger than the size of the piezoelectric layer 302 and the de-matching layer 306.

In embodiments where one or both the acoustic backing wafer 304 and the de-matching layer 306 are pre-formed, the layers 302, 306 and the wafer 304 may be laminated together using cleaning and bonding processes to form a single lamination. In embodiments where both the acoustic backing wafer 304 and the de-matching layer 306 are deposited or formed directly on the piezoelectric layer 302, a separate lamination may be optional.

Figure 3:
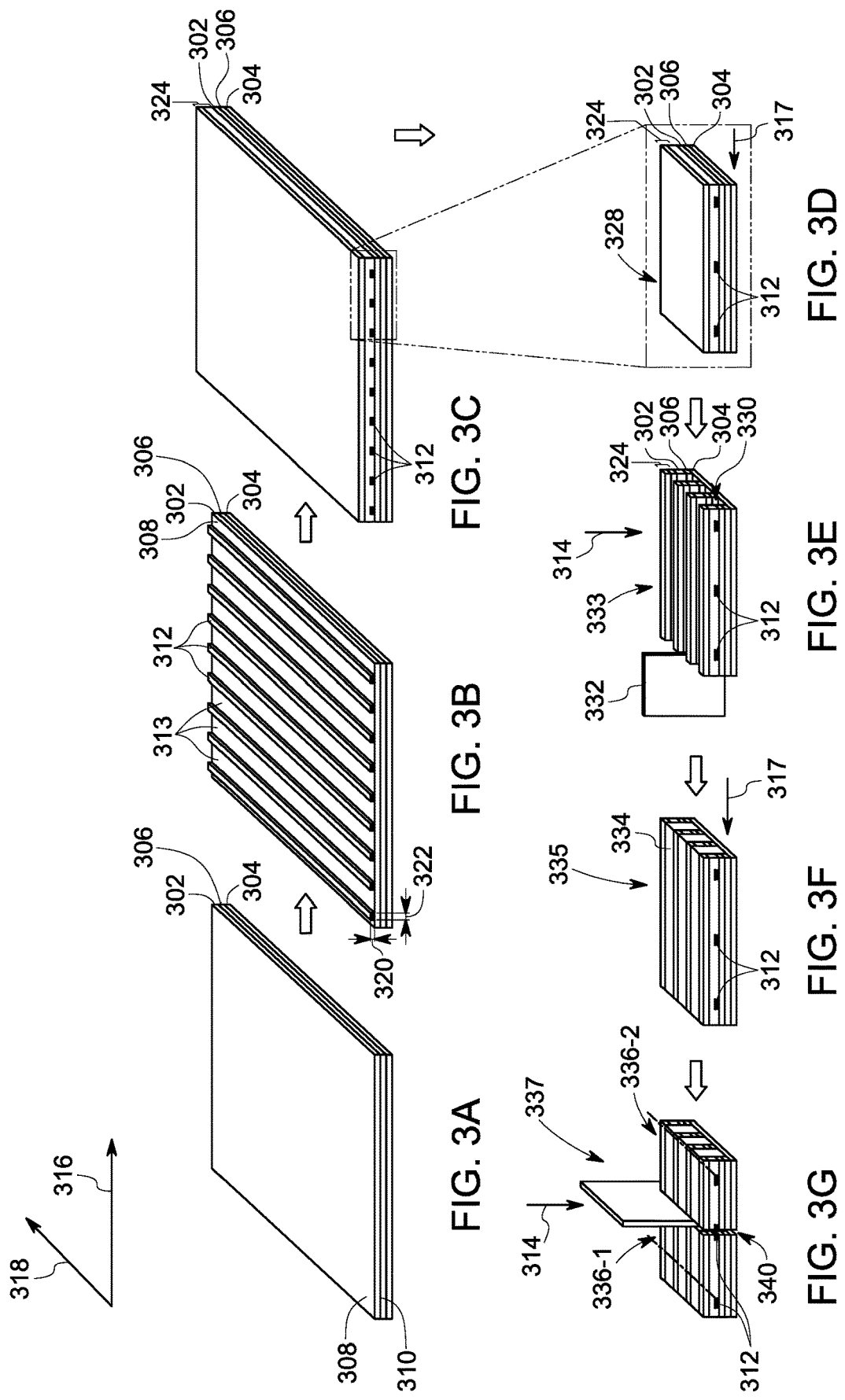
FIG. 3A-3G are schematic representations of a wafer scale method for manufacturing a grid of phased array transducers, in accordance with aspects of the present specification.

A plurality of ground contact traces 312 are deposited on the first side 308 of the piezoelectric layer 302 (see FIG. 3B). The ground contact traces 312 are used to form electrical connection between the thin metal electrodes present on the piezoelectric layer 302 and electrical traces present on an edge side of a phased array transducer so formed. Further, it may be noted that with the ground contact traces 312 disposed on the first side 308 of the piezoelectric layer 302, an electrically conductive de-matching layer, or any other electrically conductive layer may be disposed on the second side 310 of the piezoelectric layer 302 to facilitate signal routing.

The plurality of ground contact traces 312 is disposed along an elevational direction 316 on the piezoelectric layer 302 such that each ground contact trace 312 is disposed along the azimuthal direction 318 of the piezoelectric layer 302. The ground contact traces 312 are disposed in the form of conductive stripes having determined values of thickness 320 and width 322. The thickness 320 of the ground contact traces 312 should be sufficient to enable electrical contact with the electrical traces formed on the edge side of the phased array transducer. Further, the width 322 of the conductive stripes of the ground contact traces 312 should be sufficient to facilitate electrical contact with thin metal electrodes of the piezoelectric layer 302. Moreover, the width 322 of the conductive stripes of the ground contact traces 312 should be sufficient to facilitate a low electrical resistance path between the thin metal electrode of the first side 308 of the piezoelectric layer 302 and signal traces that are to be printed on the edge of the elements, after separation of individual phased array transducers, irrespective of the method that is used to separate the arrays. The signal traces may be printed on an edge side of an acoustic array stack, such that the signal traces are disposed on an edge side of the piezoelectric layer, de-matching layer, or a combination thereof.

One or more acoustic matching layers 324 may be disposed on the ground contact traces 312 (see FIG. 3C) to form an acoustic array stack. The acoustic matching layers 324 may also fill in gaps or portions 313 on the first side 308 of the piezoelectric layer 302 that are present between neighboring ground contact traces 312. Particularly, the acoustic array stack may include acoustic matching layers 324 disposed on the ground contact traces 312, as well as on the portions 313 of the first side 308 of the piezoelectric layer 302. By way of example, a material of the acoustic matching layers 324 may be disposed on the ground contact traces 312, and the same material may also at least partly fill portions 313 of the first side 308 of the piezoelectric layer 302. A surface of the acoustic matching layers 324 that is opposite to the piezoelectric layer 302 is a planar surface. In some embodiments, the acoustic matching layers 324 may be pre-formed and coupled to the ground contact traces 312 and the portions 313 of the first side 308 of the piezoelectric layer 302 disposed between the ground contact traces 312. In some of these embodiments, the pre-formed acoustic matching layers 324 may be suitably grooved to fit over the ground contact traces 312 and the portions 313 of the piezoelectric layer 302 disposed therebetween. Alternatively, the acoustic matching layer 324 is formed, such as deposited using known techniques, or additively manufactured on the ground contact traces 312 and the first side 308 of the piezoelectric layer 302.

In certain embodiments, one or more of the acoustic matching layers 324 are printed (i.e., added by additive manufacturing techniques, such as 3D printing) on the ground contact traces 312 and the first side 308 of the piezoelectric layer 302 to form an acoustic array stack. As part of the printing process, one or more matching layers 324 may be patterned, such as including "cuts" (i.e., voids or empty regions) to reduce inter-element crosstalk. The acoustic impedance, speed of sound, uniformity, and thickness of the acoustic matching layers 324 is controlled to produce a phased array transducer with good acoustic and imaging performance.

For ease of illustration, for subsequent steps only a portion 328 of the acoustic array stack is illustrated in FIG. 3D. The portion 328 of the acoustic array stack is referred to as an acoustic array stack 328. The acoustic array stack 328 is diced along an elevational direction 316 and perpendicular to the ground contact traces 312 to define individual transducer elements that are electrically isolated from one other. As illustrated in FIG. 3E, an acoustic array stack 333 thus formed includes element cuts 330 (i.e., voids or empty regions) that are formed to reduce inter-element crosstalk. Specifically, in the acoustic array stack 333 various layers including the acoustic matching layers 324, ground contact traces 312, piezoelectric layer 302, acoustic backing wafer 304, and de-matching layer 306 (if present) are at least partly diced to form element cuts 330. The element cuts 330 electrically and acoustically isolate the transducer elements from one another. The element cuts 330 are made perpendicular to the ground contact traces 312. The dicing is performed perpendicular to the surface of the piezoelectric layer 302 using, for example, a dicing blade 332.

For coarse-pitch arrays, sub-dicing may be necessary to prevent coupling between thickness and lateral modes of vibration. As used herein, the term "sub-dicing" involves dicing one element into two or more sub-elements that are mechanically de-coupled but still electrically connected as one; sub-dicing may help to control resonance modes of vibration.

Subsequent to the dicing step, as illustrated in FIG. 3F, mechanical strength and integrity is provided to the diced acoustic array stack 333 by filling the dicing cuts or kerfs 330 resulting from dicing. The kerf filler material 334 is an electrically non-conductive or insulating material. Non-limiting examples of such kerf filler materials include silicones. In certain embodiments, the properties of the kerf filler material 334 may include a low shear modulus for low acoustic crosstalk between adjacently disposed transducer elements. Further, the kerf filler material 334 also provides mechanical strength and support to the transducer elements and prevents subsequent materials from flowing into the diced kerfs. In a non-limiting example, the filler material 334 may include a low-durometer silicone.

The acoustic array stack 333 having the element cuts 330 filled with the kerf filler material 334 is referred to as an acoustic array stack 335. As illustrated in FIG. 3G, the acoustic array stack 335 is diced along the azimuthal direction 318 to form dicing cuts, such as a representative dicing cut 340. The dicing cuts 340 are parallel to the azimuthal direction 318, which is along the ground contact traces 312, and are perpendicular to the orientation of transducer elements. An acoustic array stack having the dicing cuts 340 to define individual strips 336, such as 336-1 and 336-2, which represent individual phased array transducers, is referred to as acoustic array stack 337. In certain embodiments, the individual strips 336 may be formed by dicing the acoustic array stack 337 along the azimuthal direction 318 such that one or more ground contact traces 312 or signal contact traces (not shown in FIG. 3G) are cut through and form part of one or more individual strips 336.

Reference numeral 314 represents a direction of view of the acoustic array stacks 333 (see FIG. 3E) and 337 (see FIG. 3G), as illustrated in FIGS. 7A and 7B, respectively. Further, reference numeral 317 of FIG. 3F represents a direction of view of cross-sectional views of the acoustic array stacks 328 (see FIG. 3D) and 335 (see FIG. 3F) along an elevational direction 316, as illustrated in FIGS. 9A and 9B, respectively.

Figure 4:
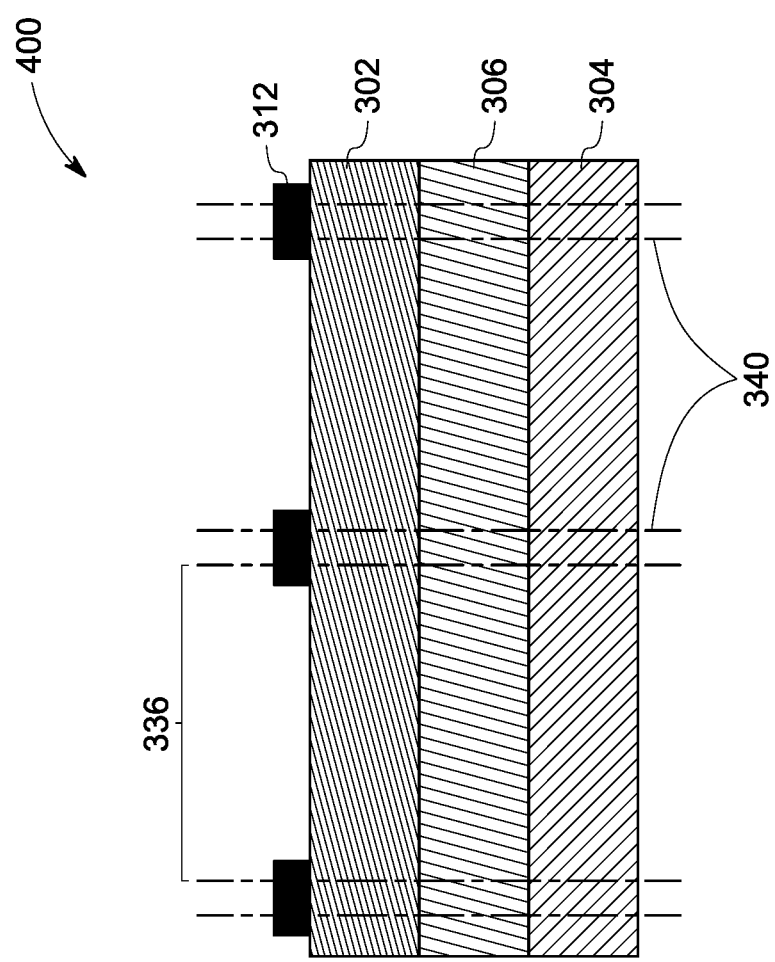
FIG. 4 is a cross-sectional side view of an acoustic array stack viewed along an azimuthal direction, where the acoustic array stack includes a grid of phased array transducers, in accordance with aspects of the present specification.

Referring to FIG. 4, a side view 400 of the acoustic array stack 337 of FIG. 3G viewed along the azimuthal direction 318 illustrates dicing cuts 340 that are made through the ground contact traces 312, piezoelectric layer 302, acoustic backing wafer 304, and de-matching layer 306 (if present) to form the individual phased array transducer strips 336. Each individual phased array transducer strip 336 may include one or more adjacently disposed individual phased array transducers along the azimuthal direction 318. Although in the illustrated embodiment, the dicing cuts 340 are shown to bisect individual ground contact traces 312, it may be noted that in alternative embodiments, the dicing cuts 340 may be positioned differently. By way of example, in one embodiment, a dicing cut may be placed adjacent a specific ground contact trace 312. The phased array transducers 336 so formed include a ground contact trace disposed along one edge. Advantageously, since the ground contact traces 312 are disposed along one or two edges of the individual phased array transducers, the ground contact traces 312 have minimal adverse effect on the acoustic performance of the corresponding phased array transducer.

In embodiments where the dicing cuts 340 cut (such as bisect) the ground contact traces 312, it is desirable for the ground contact traces 312 to be wide enough to be diced into two halves, and narrow enough to minimize adverse effect on the acoustic performance of the phased array transducers. In certain embodiments, the dicing of the cuts 340 may be deferred until after the electrical connections, such as electrical traces, are provided.

Referring now to FIGS. 5A-5D method steps subsequent to the step represented by FIG. 3G for manufacturing the grid of phased array transducers are illustrated. Specifically, FIGS. 5A-5D illustrate a flow diagram 500 for a process of forming electrical connections for the acoustic array stack 337 after filling in the filler material 334, or for individual phased array transducer strips 336. The view of FIGS. 5A-5D represent side views of one or more individual phased array transducer strips 336 of FIG. 3G viewed along the elevational direction 316. As illustrated in FIG. 5A, a carrier block 342 is attached to the acoustic backing wafer 304 of the acoustic array stack 328 or to individual phased array transducer strips 336 (if the strips are already formed). The carrier block 342 provides structural support for the acoustic array stack 328 or the individual phased array transducer strips 336.

The carrier block 342 may be attached to the acoustic array stack 328 or the individual phased array transducer strips 336 using an epoxy or other adhesive. Alternatively, the carrier block 342 may be a thermally-conductive carrier that may be coupled to the acoustic array stack 328 or the individual phased array transducer strips 336 using an adhesive.

The carrier block 342 may include features (such as, but not limited to, a projection, a hook, a particular contour, and the like) for locating or anchoring an individual phased array transducer or individual transducer assembly into a handle or head-shell to form an ultrasound transducer probe. The carrier block 342 may be used to form and/or route various electrical connections to the acoustic array stack 328. The carrier block 342 may be electrically non-conductive, or may at least have an electrically non-conductive surface. Further, it may be desirable to have a good thermal conductivity for the carrier block 342 to facilitate heat conduction away from the phased array transducer and/or the patient.

Next, electrical traces are provided on the carrier block 342. In some embodiments, the systems and methods disclosed herein use one or more electrically conducting materials or inks to form the plurality of electrical traces. The electrically conducting materials are deposited as fine electrical traces along predefined paths on the surface of the acoustic backing structure. The electrical traces may include one or more layers. Further, in some embodiments, the methods disclosed herein may also include depositing one or more electrically insulating materials or inks using additive manufacturing techniques. For example, the electrically insulating materials may be deposited between two or more electrical traces of the plurality of electrical traces, or on at least a portion of selected electrical traces, or both, to provide desirable electrical isolation to the electrical traces. Additionally, or alternatively, the electrically insulating materials may be deposited between the electrical traces and the electrodes of the phased array transducer. By way of example, the electrically insulating materials may be deposited between the signal traces and ground electrodes. In one example, a direct write technology may be used to deposit the electrically conducting inks and/or electrically insulating inks.

In some embodiments, the electrical traces are additively printed on determined portions on an edge side 344 of the carrier block 342. First, a plurality of signal traces 346 are printed on the edge side 344 of the carrier block 342 (see FIG. 5B). The plurality of signal traces 346 is printed such that the signal traces 346 provide electrical connection with the electrically conductive de-matching layer 306, in embodiments where the de-matching layer 306 is present between the piezoelectric layer 302 and the acoustic backing wafer 304. The signal traces 346 provide electrical connection between the transducer elements and the electrical connector located outside the transducer assembly. The de-matching layer 306 is electrically coupled to the thin metal electrodes disposed on the second side 310 of the piezoelectric layer 302, hence the signal traces 346 provide electrical or signal connections to the individual transducer elements of the piezoelectric layer 302. Since the transducer elements are electrically isolated (by dicing the acoustic array stack 328 in the elevational direction 316), a respective signal trace 346 is needed for each transducer element of the plurality of transducer elements.

In certain implementations, the signals traces 346 may be fabricated using additive manufacturing/printing processes (such as controlled dispensing, jetting, and so forth) and curing of a highly conductive ink (e.g., nanoparticle- or organometallic-based silver, copper, or gold) on the acoustic backing wafer 304, and the carrier block 342 and/or may be laser-structured on the acoustic backing wafer 304, and the carrier block 342.

In certain embodiments, a sub-dice step may also be performed. If the elements are sub-diced, the signal traces must connect to all sub-elements. Sub-dicing may help to control resonance modes of vibration. By way of example, in one implementation, a sub-dice step may be performed through the piezoelectric layer 302 and de-matching layer 306 to help control resonance modes.

The signal traces 346 may be routed on the two edge sides only where the ground contact traces 312 run parallel to the edge sides of the acoustic array stack 328 or the phased array transducer strips 336. In some embodiments, the signal traces 346 may be routed on a single edge side 344. In alternative embodiments, the signal traces 346 may be divided between two opposing sides of the stack 328 or the strip 336.

After printing the signal traces 346, an electrically insulating or dielectric layer 350 is disposed on at least portions of the de-matching layer 306 (if the de-matching layer is present), the piezoelectric layer 302, or both that are exposed and disposed between the signal traces 346 (see FIG. 5C). Alternatively, the dielectric layer 350 may be disposed on the de-matching layer 306 or the piezoelectric layer 302, or both as well as on the signal traces 346, as illustrated. In some embodiments, the dielectric layer 350 may be printed over an exposed edge side of the one or more signal contact traces, de-matching layer, a portion of the piezoelectric layer, or combinations thereof.

Next, a plurality of ground traces 352 is routed or printed on the edge side of the carrier block 342, acoustic backing wafer 304, and dielectric layer 350 such that the ground traces 352 are electrically coupled to the ground contact traces 312 (see FIG. 5D). The ground traces 352 are electrically coupled to each transducer element of the plurality of transducer elements of each phased array transducer to provide a ground connection to each of the transducer elements. The ground traces 352 may be disposed on one or both of the opposite edge sides 344 of the stack 328 or the strip 336 having the ground contact traces 312 disposed along a perimeter of a surface of the first side 308 of the piezoelectric layer 302. The ground traces 352 are further connected to an external electrical connector like the signal traces 346. The dielectric layer 350 may be additively manufactured on at least a portion of signal electrodes to electrically isolate the plurality of ground traces 352 from the one or more signal electrodes.

In embodiments where the signal traces 346 for the odd and even-numbered transducer elements are printed on opposite edge sides, and the ground traces 352 are routed on two edge sides, the ground traces 352 for the odd-numbered transducer elements may be routed on the same edge side as the signal traces for the even-numbered transducer elements, and vice versa.

Optionally, as illustrated in FIG. 5D a ground bus 354 may be formed along an edge side 344 of the strip of an individual phased array transducer such that the ground bus 354 is disposed on the acoustic backing 304 or carrier block 342 and creates an electrical connection between the ground traces 352. At this stage, if individual phased array transducer strips not already diced, individual phased array transducer strips and arrays may be formed at this stage.

Certain other steps that may be carried out to form the phased array transducer include adding an acoustic lens, for focusing in the elevational direction 316, to an individual phased array transducer. The acoustic lens may be coupled to the individual phased array transducer by using a suitable adhesive to couple a pre-molded lens on the phased array transducer. Alternatively, the phased array transducer may be mounted in a head-shell for a transducer probe and subsequently a cast-in-place lens may be formed on the phased array transducer by using existing methods and processes. Before cutting the wafer into strips or individual phased array transducers, in one embodiment, a suitable mold may be used to cast an array of lenses on the piezoelectric wafer 302 of the phased array transducers, after the matching layers and element dicing.

Next, electrical connections from the phased array transducer may be connected to a test cable for testing purposes, and electrical and acoustic tests may be performed. After the tests are conducted successfully, the transducer may be coupled to a cable assembly to form the transducer probe. Electrical shields, heat transfer materials, and the like may be added suitably. If the array is not previously installed in a head-shell, the array may be installed in the head-shell at this stage. Sealing and safety testing including assessing electrical, acoustic and imaging functionalities may also be carried out at this point.

FIGS. 6A-6L illustrate a method of making a grid of phased array transducers, where the phased array transducers of the grid do not employ a de-matching layer between a piezoelectric layer 702 and an acoustic backing layer or wafer 704. Further, the method of FIGS. 6A-6L obviates the need for acoustic laminations.

The method starts by providing the piezoelectric layer 702 having a desired thickness based on for example, frequency of operation of the resultant transducer. As illustrated in FIG. 6A, in some embodiments, a plurality of ground contact traces 712 is pre-deposited on the first side 708 of the piezoelectric layer 702. However, as illustrated in FIGS. 6B and 6C, in some other embodiments, the plurality of ground contact traces 712 may be deposited on the first side 708 of the piezoelectric layer 702 after disposing an acoustic backing wafer 704 on the second side 710 of the piezoelectric layer 702. The ground contact traces 712 are used to form electrical connection between the thin metal electrodes present on the piezoelectric layer 702 and electrical traces present on an edge side of a phased array transducer so formed.

As with the piezoelectric layer 302 of FIGS. 3A-3G, the piezoelectric layer 702 may be made of a single crystal of piezoelectric material or may be made of a piezoelectric ceramic material and have a suitable thickness. Further, reference numerals 708 and 710 represent two surfaces or faces of the piezoelectric layer 702 that are metallized to form thin metal electrodes. In one example, an adhesion layer may be sputter deposited followed by a sputtered layer of gold. Size of the piezoelectric layer 702 may be determined based on the number and size of individual phased array transducers.

Figure 6J:
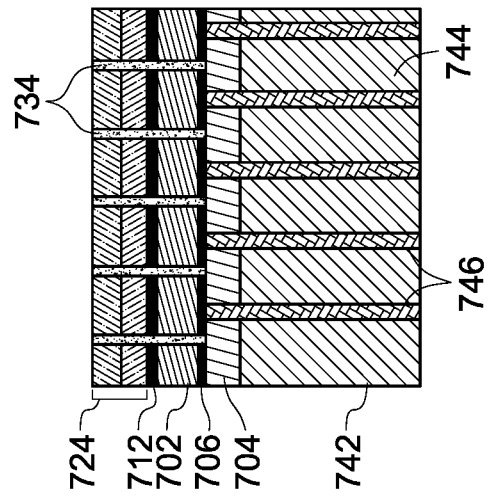
Figure 6L:
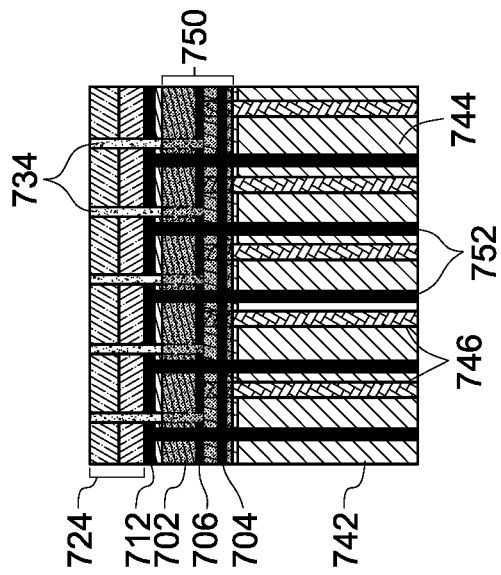

As illustrated in FIG. 6B, signal contact traces 706 are disposed on the second side 710 of the piezoelectric layer 702. The signal contact traces 706 are used to connect the thin metal electrodes present on the second side 710 of the piezoelectric layer 702 to signal traces. Consequently, the signal contact traces 706 are wide enough to facilitate good electrical contact to a signal electrode on the piezoelectric layer 702. Further, the signal contact traces 706 are thick enough to make good electrical contact with the signal traces that are subsequently deposited on an edge side of the phased array transducer. The signal contact traces 706 are configured to perform a similar function of providing electrical connection as the de-matching layer 306 in FIGS. 3A-3G. Hence, in the presently contemplated embodiment of FIGS. 6A-6L, a de-matching layer is not required. The presence or absence of the de-matching layer is due to different acoustic designs. In other words, in addition to providing electrical connection to the piezoelectric layer, the de-matching layer also performs an acoustic purpose. Therefore, for acoustic designs that do not require a de-matching layer, signal contact traces, such as traces 706, are used to provide an element that has sufficiently large physical dimensions and is robust to facilitate electrical connection of the edge traces that are subsequently printed.

Like the acoustic backing wafer 304 of FIGS. 3A-3G, the acoustic backing wafer 704 is made of materials having suitable acoustic and mechanical properties. Further, the acoustic backing wafer 704 may have a suitable thickness to provide mechanical strength to the phased array transducer. The material of the acoustic backing wafer 704 may include a composite material having acoustic scattering materials or particles, such as, but not limited to, tungsten particles, phenolic microspheres, and the like. Alternatively, the acoustic backing wafer 704 may be directly formed, such as deposited using known deposition techniques, or additively manufactured on the second side 710 of the piezoelectric layer 702.

Similar to the ground contact traces 312 of FIGS. 3B-3G, the plurality of ground contact traces 712 is disposed along an elevational direction 716 on the piezoelectric layer 702 such that each individual ground contact trace 712 is disposed along the azimuthal direction 718 of the piezoelectric layer 702. Further, the ground contact traces 712 may be similar to the ground contact traces 312 of FIGS. 3B-3G. In particular, dimensions, materials, orientation, and the like of the ground contact traces 712 are similar to that of the traces 312 of FIGS. 3B-3G. Moreover, the signal contact traces 706 may be similar in dimensions, materials, and orientation to the ground contact traces 712. In some embodiments, the ground contact traces 712 are aligned with the signal contact traces 706 of the piezoelectric layer 702. Alternatively, in some other embodiments, the ground and signal contact traces 712 and 706, respectively, may be offset such that when the acoustic array stack is diced into (strips of) individual phased array transducers, a ground contact trace 712 is exposed along one edge and a corresponding signal contact trace 706 is exposed along the opposite edge of each (strip of) phased array transducer(s). In some of these embodiments, the signal and ground contact traces 706 and 712, respectively, may be disposed at 2× the elevation of the finished arrays, and offset by 1× the elevation. The dicing cuts split every signal and ground contact trace. The resulting (strips of) arrays are mirror symmetric. Alternatively, narrower signal and ground contact traces may be disposed at 1× the elevation, offset so that the signal and ground contact traces are adjacent but not overlapping. The dicing cut goes between them, so a signal contact trace is exposed on one side of the dicing cut and a ground contact trace is exposed on the opposite side of the same cut. The resulting (strips of) arrays are identical (have translational symmetry).

As illustrated in FIG. 6D, one or more acoustic matching layers 724, similar to the acoustic matching layers 324, may be disposed on the ground contact traces 712 to form an acoustic array stack. The process of disposing the acoustic matching layers 724 is similar to the process described with respect to the acoustic matching layers 324.

As illustrated in FIG. 6F, a portion 728 of the acoustic array stack of FIG. 6D, is diced along an elevational direction 716 and perpendicular to the ground contact traces 712 to define individual transducer elements that are electrically isolated from one other. The dicing is performed perpendicular to the surface of the piezoelectric layer 702 using, for example, a dicing blade 732. An acoustic array stack 733 thus formed includes element cuts 730 that are formed to reduce inter-element crosstalk.

Further, as illustrated in FIG. 6G, the acoustic array stack 733 is filled with a kerf material 734 to form an acoustic array stack 735. Moreover, as illustrated in FIG. 6H, the stack 735 having the kerf material 734 is diced in the azimuthal direction 718 to form dicing cuts 740 to define individual strips 736, such as 736-1 and 736-2, which represent individual phased array transducers. The acoustic array stack of FIG. 6F is referred to as an acoustic array stack 737.

Figure 6I:
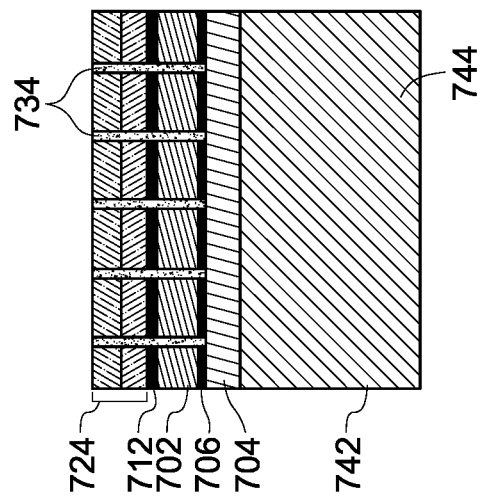
Figure 6K:
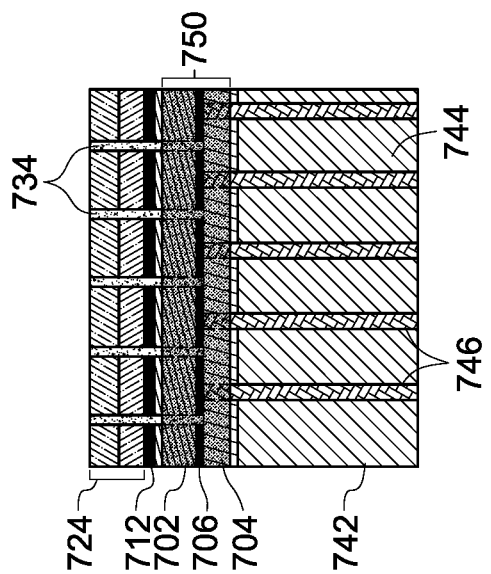

As illustrated in FIG. 6I, a carrier block 742 is attached to the acoustic backing wafer 704. Further, as illustrated in FIG. 6J, signal traces 746 are disposed on an edge side 744 of the carrier block 742. Further, the signal traces 746 are electrically coupled to the signal contact traces 706 disposed on the second side 710 of the piezoelectric layer 702. Subsequently, a dielectric layer 750 is disposed on at least portions of the piezoelectric layer 702 and signal contact traces 706 disposed on the second side 710 of the piezoelectric layer 702. Next, a plurality of ground traces 752 is routed or printed on the edge side 744 of the carrier block 742, acoustic backing wafer 704, and dielectric layer 750 such that the ground traces 752 are electrically coupled to the ground contact traces 712. In certain embodiments, the plurality of signal traces 746 may be printed on the edge side 744 of the acoustic array stack, such that the signal traces 746 are disposed on an edge side of the piezoelectric layer 702, one or more signal contact traces 706, a de-matching layer, or combinations thereof.

The electrical traces 746 and 752 and the dielectric layer 750 are similar to the electrical traces 346 and 352 and dielectric layer 350, respectively, as described with respect to FIGS. 5B-5D. Further, materials, deposition techniques of the electrical traces 746 and 752 and the dielectric layer 750 are similar to that of the ones described with respect to FIGS. 5C-5D.

Moreover, the rest of the steps pertaining to forming an ultrasound transducer probe may be performed in a similar manner as described with respect to FIGS. 3A-3G and 5A-5D.

FIGS. 7A-7B, 8, and 9A-9B illustrate a wafer scale manufacturing process for forming a grid of phased array transducers having a de-matching layer and a boundary ground bus. The process of FIGS. 7A-7B is similar to the process of FIGS. 3A-3G till the step of filling kerf material in the dicing cuts made in elevational direction in the acoustic array stack 328. Like reference numerals are used to represent like parts of FIGS. 3A-3G, 7A-7B and 9A-9B.

FIGS. 7A and 7B represent top views seen in the direction of arrows 314 of the acoustic array stacks 333 and 337 of FIGS. 3E and 3G, respectively. FIG. 8 represents a side view of the same acoustic array stack 328 seen in an azimuthal direction 318. FIGS. 9A-9B represent cross-sectional side views of the acoustic array stacks 328 and 335 of FIGS. 3D and 3F, respectively, seen in an elevational direction 316 as represented by arrow 317 (see FIG. 3F).

Turning now to FIGS. 7A-7B, width 322 of the ground contact traces 312 is sufficient enough to allow formation of dicing cuts, filling of electrically conductive filler material and subsequent singulation of phased array transducer strips. As illustrated, dicing cuts 340 and 341 are made in elevational 318 and azimuthal 316 directions, respectively. The dicing cuts define individual phased array transducers. The cuts 340 and 341 are subsequently filled with electrically conductive filler material. A non-limiting example of the electrically conductive filler material includes silver epoxy which fills the wide cuts 340 and 341. The cuts 340 and 341 are wide enough so that when the subsequent cut is made to singulate the phased array transducers (along the dashed lines X and Y), there is sufficient width, w, available for the remaining conductive filler on each phased array transducer to form a low resistance ground bus that wraps around the outer perimeter of the phased array transducer. In a non-limiting example, the width of the cuts 340 and 341 may be in a range of 50 microns to 1000 microns. In another non-limiting example, the width of the cuts 340 and 341 may be over 1000 microns.

As illustrated in FIGS. 10 and 11, the cuts 340 and 341 are made deep enough to expose the ground contact traces 312 and end within the thickness of the piezoelectric layer 302. It should be noted that the cuts 340 and 341 do not exceed beyond the thickness of the piezoelectric layer 302. The cuts 340 and 341 do not expose the thin metal electrodes disposed on the second side 310 of the piezoelectric layer 302. The cuts 340 and 341 are filled with filler material 343 that is an electrically conductive material, such as, but not limited to, a metal-filled epoxy (e.g., silver epoxy). In a non-limiting example, this filling of the cuts 340 and 341 may be performed using a syringe-based epoxy dispenser.

After filling the cuts 340 and 341 with the electrically conductive filler material, individual phased array transducers may be singulated or diced out by dicing individual transducers 362 (see FIG. 9B) out of a grid 360 of individual phased array transducers 362. The dicing of the transducers 362 may be performed by cutting through the filler material 343 such that the filler material 343 is exposed upon dicing the individual transducers 362.

The resultant phased array transducer 362 includes the electrically conductive filler material 343 disposed around the outer perimeter of each of the transducer 362 till the level of the cuts 340 and 341. This conductive filler material 343 forms a boundary ground bus around the outer perimeter for each individual transducer 362. It may be noted that while in some embodiments, the conductive filler material 343 may be disposed on all 4 sides of the perimeter, in some other embodiments, the conductive filler material 343 may be disposed on 2 adjacent sides (i.e. one elevational side and one azimuthal side.

Next a carrier block (not shown in FIGS. 9A-9B) is coupled to the phased array transducer 362. Further, signal traces 346 (see FIG. 10), are disposed on portions of the carrier block, piezoelectric layer 302, de-matching layer, as described with respect to FIG. 5.

FIGS. 10-11 represent two side views of a single phased array transducer 1200 formed using the method of FIGS. 7A-7B and 9A-9B. In FIGS. 10-11, to enable clear depiction of the electrical traces 346 and 352, a carrier block is not illustrated. FIG. 10 illustrates the phased array transducer 1200 along the azimuthal direction and FIG. 11 shows the phased array transducer 1200 along the elevational direction.

For phased array transducers 362 (see FIG. 9B) with functional elements on each end, an electrical insulator 350 (see FIG. 11) may be printed or deposited over the piezoelectric layer 302 and the de-matching layer 306 prior to printing/depositing the ground traces 352 that connect to the boundary ground bus. It may be noted that one or more phased array transducers 362 include one or two dummy elements at each end to provide first and last functional elements with the same mechanical boundary conditions as the elements in the center of the array. It may be noted that for the grids 360 with dummy elements on the ends of the array, it is not necessary to print/deposit the electrical insulator 350 prior to printing the ground traces 352 over the piezoelectric layer 302 and the de-matching layer 304.

Technical effects of the specification include the bulk manufacture of a grid of phased array transducers. In one implementation, by producing multiple arrays at once on a common carrier, and by using direct-deposit additive processes for the matching layers and the signal and ground electrical connections, the described process greatly reduces the number of parts and the number of manual operations. This process should be capable of partial or full automation, which should dramatically increase production capacity and reduce product cost.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A wafer scale method for manufacturing a grid of phased array transducers comprising:
providing a piezoelectric layer having a first side and a second side, wherein the piezoelectric layer comprises a piezoelectric material with a first metallized surface on the first side and second metallized surface on the second side, wherein the first metallized surface is directly applied to the piezoelectric material and the second metallized surface is directly applied to the piezoelectric material, wherein the first metallized surface forms a ground electrode and the second metallized surface forms a signal electrode;
forming a plurality of ground contact traces along an elevational direction on the first side of the piezoelectric layer to define an acoustic array stack, wherein each of the plurality of ground contact traces is in electrical contact with the first metallized surface and extends along an azimuthal direction, wherein each of the plurality of ground contact traces has a width in the elevational direction that is less than 10% of a center-to-center distance between any two of the plurality of ground contact traces in the elevational direction;

dicing the acoustic array stack along the elevational direction perpendicular to the ground contact traces to define individual transducer elements that are electrically isolated from one another;

dicing the acoustic array stack along the azimuthal direction through the ground contact traces to define strips of phased array transducers such that at least a portion of each of the plurality of ground contact traces is exposed along a side of the strips of the phased array transducers;

coupling a carrier block to at least a portion of the acoustic array stack;

disposing a de-matching layer on the second side of the piezoelectric layer, wherein the de-matching layer is in contact with the metallized second surface; and disposing one or more acoustic matching layers on the first side of the piezoelectric layer, wherein one of the one or more acoustic matching layers is in contact with both the plurality of ground contact traces and the first metallized surface.

2. The wafer scale method of claim 1, further comprising filling element dicing kerfs to provide mechanical support to a plurality of transducer elements of the phased array transducers, before dicing the acoustic array stack along the azimuthal direction.

3. The wafer scale method of claim 1, further comprising printing a plurality of signal traces on an edge side of the acoustic array stack, such that the signal traces are disposed on an edge side of the piezoelectric layer, one or more signal contact traces, the de-matching layer, or a combination thereof.

4. The wafer scale method of claim 1, further comprising printing a dielectric layer over an edge side of one or more ground contact traces, the de-matching layer, a portion of the piezoelectric layer, or combinations thereof.

5. The wafer scale method of claim 4, further comprising printing ground traces on the plurality of ground contact traces and the edge side of the piezoelectric layer, the dielectric layer, and carrier block.

6. The wafer scale method of claim 1, further comprising printing a plurality of electrical traces routed on a surface of the carrier block and operatively coupled to at least one or more signal electrodes, and one or more ground electrodes, and wherein the plurality of electrical traces comprises a plurality of signal traces and a plurality of ground traces.

7. The wafer scale method of claim 6, further comprising electrically coupling the plurality of signal traces to respective signal electrodes of the one or more signal electrodes.

8. The wafer scale method of claim 7, further comprising additively manufacturing an electrically insulating material layer on at least a portion of the signal electrodes to electrically isolate the plurality of ground traces from the one or more signal electrodes.

9. The wafer scale method of claim 1, wherein dicing the acoustic array stack along the azimuthal direction comprises cutting one or more of the plurality of ground contact traces.

10. The wafer scale method of claim 9, further comprising filling dicing cuts made in elevational and azimuthal directions with an electrically conductive filler material, wherein the dicing cuts define individual phased array transducers.

* * * * *